(12) United States Patent
Fukuda

(10) Patent No.: US 10,806,335 B2
(45) Date of Patent: Oct. 20, 2020

(54) ENDOSCOPE SYSTEM

(71) Applicant: HOYA CORPORATION, Tokyo (JP)

(72) Inventor: Masaaki Fukuda, Tokyo (JP)

(73) Assignee: HOYA CORPORATION, Tokyo (JP)

(*) Notice: Subject to any disclaimer, the term of this patent is extended or adjusted under 35 U.S.C. 154(b) by 24 days.

(21) Appl. No.: 16/318,280

(22) PCT Filed: Sep. 1, 2017

(86) PCT No.: PCT/JP2017/031673
§ 371 (c)(1),
(2) Date: Jan. 16, 2019

(87) PCT Pub. No.: WO2018/043726
PCT Pub. Date: Mar. 8, 2018

(65) Prior Publication Data
US 2019/0216305 A1    Jul. 18, 2019

(30) Foreign Application Priority Data

Sep. 2, 2016 (JP) .................................. 2016-171950

(51) Int. Cl.
*G06T 7/00* (2017.01)
*A61B 1/06* (2006.01)
(Continued)

(52) U.S. Cl.
CPC .............. *A61B 1/0638* (2013.01); *A61B 1/00* (2013.01); *A61B 1/045* (2013.01); *A61B 1/0676* (2013.01);
(Continued)

(58) Field of Classification Search
CPC ......... G06T 2207/10068; G06T 7/0012; G06T 2207/10024; G06T 2207/10152;
(Continued)

(56) References Cited

U.S. PATENT DOCUMENTS

2013/0030268 A1* 1/2013 Saito ........................ A61B 1/05
                                                         600/325
2015/0216460 A1* 8/2015 Shigeta ...................... A61B 1/05
                                                         600/339
(Continued)

FOREIGN PATENT DOCUMENTS

| JP | H09-173285 A | 7/1997 |
| JP | 2013-240401 A | 12/2013 |
| JP | 2015-160012 A | 9/2015 |

OTHER PUBLICATIONS

PCT/JP2017/031673 International Search Report, dated Nov. 7, 2017.

*Primary Examiner* — Quan M Hua
(74) *Attorney, Agent, or Firm* — Kilpatrick Townsend & Stockton LLP

(57) ABSTRACT

A processor of an endoscope system uses components of color image data of biological tissue illuminated by at least two types of light to generate an oxygen saturation distribution image of hemoglobin in the biological tissue and to calculate a certainty of an oxygen saturation. Furthermore, the processor controls a display mode of the oxygen saturation distribution image according to the degree of the certainty. The certainty drops if the value of a first component a of the color image data is lower than a lower limit threshold value. The certainty drops if the value of a second component b of the color image data is greater than an upper limit threshold value. The lower limit threshold value and the upper limit threshold value are values of two different pieces of color image data.

20 Claims, 6 Drawing Sheets

(51) Int. Cl.
  *A61B 1/045* (2006.01)
  *A61B 1/00* (2006.01)
  *G02B 23/24* (2006.01)
(52) U.S. Cl.
  CPC ......... *G02B 23/24* (2013.01); *G02B 23/2461*
    (2013.01); *A61B 1/0008* (2013.01); *A61B*
    *1/00009* (2013.01)
(58) Field of Classification Search
  CPC . G06T 2207/30101; G06T 2207/10016; G06T
    5/008; G06T 2207/20221; G06T
    2207/30024; G06T 5/50; G06T 11/001;
    G06T 2207/10064; G06T 2207/30004;
    G06T 2207/30028; G06T 2207/30092;
    G06T 2207/30096; G06T 5/007; G06T
    7/62; G06T 2207/20212; G06T
    2207/20224
  See application file for complete search history.

(56) References Cited

U.S. PATENT DOCUMENTS

2015/0238086 A1    8/2015  Saito
2016/0353972 A1*  12/2016  Yano .................... H04N 5/2256

\* cited by examiner

ENDOSCOPE SYSTEM

CROSS-REFERENCE TO RELATED APPLICATIONS

This application is a 371 U.S. National Phase of PCT International Application No. PCT/JP2017/031673 filed on Sep. 1, 2017, which claims benefit and priority to Japanese patent application No. 2016-171950 filed on Sep. 2, 2016, and which is incorporated by reference herein in its entirety.

TECHNICAL FIELD

The present disclosure relates to an endoscope system that performs image display of biological information in biological tissue based on image data generated by imaging the biological tissue.

BACKGROUND ART

An endoscope system has been known which includes a function of obtaining information on a biological substance in biological tissue, which is an imaging subject, such as information on an amount of hemoglobin and an oxygen saturation of hemoglobin, based on image data obtained by an endoscope, and performing image display. An example of this kind of endoscope system is disclosed in Patent Document 1.

The endoscope system disclosed in Patent Document 1 includes: an imaging means for obtaining spectral image data by capturing a spectroscopic image of a predetermined wavelength region in a body cavity; a processing means for performing predetermined processing on the spectral image data to generate composite image data in which a characteristic amount of the biological tissue, such as the oxygen saturation, is emphasized; and a display means for performing screen display based on the composite image data. The endoscope system can display the composite image as an image for specifying a lesioned part as distinguished from a healthy part.

CITATION LIST

Patent Documents

Patent Document 1: JP 2013-240401A

SUMMARY OF DISCLOSURE

Technical Problem

The above-described endoscope system can help an operator judge and specify whether or not there is a lesioned part such as a malignant tumor, and its position, using an oxygen saturation distribution image showing a distribution of a characteristic amount of the biological tissue, such as oxygen saturation, which is displayed on the display. The oxygen saturation is calculated based on the image data of the biological tissue through predetermined processing, and therefore even at a part at which the value of the oxygen saturation is not deemed to be an abnormal value, pixel values that are very small, very large, or the like in the processing exist in some cases. It can be said that the certainty of the oxygen saturation at such a part is intrinsically low.

For this reason, when the operator judges whether or not there is a lesioned part and specifies its position, with the endoscope system, it is preferable that parts at which the certainty of the calculated oxygen saturation is high are displayed on the display. Also, it is preferable that when information on the certainty of the oxygen saturation is obtained based on the image data, the information on the certainty is obtained by efficiently using the image data such that the obtained information on the certainty is not excessive.

The present disclosure has been made in view of the foregoing circumstance, and it is an object thereof to provide an endoscope system according to which, when displaying an oxygen saturation distribution image on a display, the oxygen saturation distribution image indicating a distribution of the oxygen saturation of hemoglobin in biological tissue obtained using image data of the biological tissue obtained by illuminating and imaging the biological tissue, it is possible to efficiently obtain information on the certainty of the oxygen saturation and display a highly-accurate oxygen saturation distribution image.

Solution to the Problem

The present disclosure includes the following aspects.
Aspect 1
An endoscope system including:
  a light source apparatus configured to emit at least two types of light with different wavelength bands;
  an endoscope including an imaging unit that includes an image sensor configured to generate a plurality of pieces of color image data corresponding to the at least two types of light by imaging biological tissue illuminated with the types of light;
  a processor including: a characteristic amount acquisition unit configured to acquire an oxygen saturation of hemoglobin in the biological tissue as a characteristic amount of the biological tissue using at least a component a and a component b among components of the color image data, and to generate an oxygen saturation distribution image showing a distribution of the characteristic amount; a certainty calculation unit configured to calculate a certainty of the characteristic amount using the components of the color image data; and an image display control unit configured to control a mode of displaying the oxygen saturation distribution image according to a result of calculating the certainty; and
  an image display apparatus configured to display the oxygen saturation distribution image,
  wherein the certainty calculation unit is configured to calculate the certainty in a state in which a first value of a component a of color image data A of the color image data is set as a certainty lower limit threshold value at which the certainty falls below the certainty at a value greater than or equal to the first value if the value of the component a of the color image data A is lower than the first value, and a second value, which is greater than the first value, of a component b of color image data B of the color image data is set as a certainty upper limit threshold value at which the certainty falls below the certainty at a value less than or equal to the second value if the value of the component b of the color image data B is greater, and the color image data A and the color image data B are pieces of color image data corresponding to the two different types of light.

Aspect 2
  The endoscope system according to Aspect 1, wherein
    the certainty calculation unit is configured to calculate the certainty for each pixel based on certainty components based on each of the component a and the component b,
    if the value of the component of the color image data A is greater than the certainty lower limit threshold value, the certainty component obtained based on the color image data A has a value that is the same as or greater than the certainty component at the certainty lower limit threshold value, and
    if the value of the component of the color image data B is smaller than the certainty upper limit threshold value, the certainty component obtained based on the color image data B has a value that is the same as or greater than the certainty at the certainty upper limit threshold value.

Aspect 3
  The endoscope system according to Aspect 1 or 2, wherein
    the characteristic amount acquisition unit includes: a hemoglobin amount calculation unit configured to calculate an amount of the hemoglobin based on a first ratio obtained using a component including at least one of the component a and the component b of the color image data; and an oxygen saturation calculation unit configured to calculate an oxygen saturation of the hemoglobin based on the amount of the hemoglobin and a second ratio obtained using a component including at least one of the component a and the component b of the color image data, and
    the certainty calculation unit is configured to perform correction such that the certainty decreases when the first ratio falls outside of a predetermined range.

Aspect 4
  The endoscope system according to any one of Aspects 1 to 3, wherein
    the characteristic amount acquisition unit includes: a hemoglobin amount calculation unit configured to calculate an amount of the hemoglobin based on a first ratio obtained using a component including at least one of the component a and the component b of the color image data; and an oxygen saturation calculation unit configured to calculate an oxygen saturation of the hemoglobin based on the amount of the hemoglobin and a second region obtained using a component including at least one of the component a and the component b of the color image data, and
    the certainty calculation unit is configured to perform correction such that the certainty decreases when the second ratio falls outside of a predetermined range.

Aspect 5
  The endoscope system according to Aspect 3 or 4, wherein the image display control unit performs control such that the image of the distribution of the characteristic amounts is displayed superimposed on the image of the biological tissue, and is configured to adjust a transparency of a pixel in which the value of the second ratio falls outside of an allowable range of the second ratio determined according to the amount of the hemoglobin.

Aspect 6
  The endoscope system according Aspect 3, wherein
    the light source apparatus is configured to emit at least three or more types of light including a first light, a second light, and a third light with different wavelength bands,
    the imaging unit is configured to generate first color image data corresponding to the first light, second color image data corresponding to the second light, and third color image data corresponding to the third light by imaging biological tissue illuminated with the first light, the second light, and the third light,
    the first ratio is a ratio between one component of the first color image data and one component of the second color image data, and
    the second ratio is a ratio between one component of the second color image data and one component of the third color image data.

Aspect 7
  The endoscope system according to Aspect 6, wherein
    the wavelength band of the first light is wider than the wavelength band of the second light and the wavelength band of the third light, and the wavelength band of the second light is wider than the wavelength band of the third light, and
    the certainty upper limit threshold value is a value of a luminance component of the first color image data or the second color image data, and the certainty lower limit threshold value is a value of a luminance component of the third color image data.

Aspect 8
  The endoscope system according to Aspect 6 or 7, wherein
    the first ratio is a ratio between the luminance component of the second color image data and an R component or a sum of an R component and a G component of the first color image data, and
    the hemoglobin amount calculation unit calculates the amount of the hemoglobin based on the first ratio.

Aspect 9
  The endoscope system according to any one of Aspects 6 to 8, wherein
    the second ratio is a ratio between the luminance component of the third color image data and a luminance component of the second color image data, and
    the oxygen saturation calculation unit calculates the oxygen saturation of the hemoglobin based on the second ratio and the amount of the hemoglobin.

Aspect 10
  The endoscope system according to any one of Aspects 6 to 9, wherein in the wavelength band of the second light, a component of the second color image data includes a wavelength band that is sensitive to change in the hemoglobin amount of the biological tissue but is not sensitive to change in the oxygen saturation.

Aspect 11
  The endoscope system according to any one of Aspects 6 to 10, wherein in the wavelength band of the third light, a component of the third color image data includes a wavelength band that is sensitive to change in the oxygen saturation.

Aspect 12
  The endoscope system according to any one of Aspects 6 to 11, wherein the second light is filtered light of the first light, obtained by an optical filter allowing transmission of a first wavelength band in a range of 500 nm to 600 nm in the wavelength band of the first light, and the third light is filtered light of the first light, obtained by an optical filter allowing transmission of a second wavelength band that is narrower than the first wavelength band in the range of the first wavelength band.

Aspect 13
An endoscope system including;
a light source apparatus configured to emit a first light including at least two light components with different wavelength bands;
an endoscope including an imaging unit that includes an image sensor configured to generate first color image data by imaging biological tissue illuminated with the first light;
a processor including; a characteristic amount acquisition unit configured to acquire an oxygen saturation of hemoglobin in the biological tissue as a characteristic amount of the biological tissue using at least a component a and a component b among corresponding components of the first color image data, which correspond to respective wavelength bands of the light components, and to generate an oxygen saturation distribution image showing a distribution of the characteristic amount; a certainty calculation unit configured to calculate a certainty of the characteristic amount using the corresponding components of the color image data; and an image display control unit configured to control a mode of displaying the oxygen saturation distribution image according to a result of calculating the certainty; and
an image display apparatus configured to display the oxygen saturation distribution image,
wherein the certainty calculation unit is configured to calculate the certainty in a state in which a first value of the component a is set as a certainty lower limit threshold value at which the certainty falls below the certainty at a value greater than or equal to the first value if the value of the component a is lower than the first value, and a second value, which is greater than the first value, of the component b is set as a certainty upper limit threshold value at which the certainty falls below the certainty at a value less than or equal to the second value if the value of the component b is greater, and the component a and the component b are two corresponding components that are different from each other.

Aspect 14
The endoscope system according to Aspect 13, wherein the certainty calculation unit is configured to calculate the certainty for each pixel based on certainty components based on each of the component a and the component b,
if the value of the component a is greater than the certainty lower limit threshold value, the certainty component obtained based on the component a has a value that is the same as or greater than the certainty component at the certainty lower limit threshold value, and
if the value of the component b is smaller than the certainty upper limit threshold value, the certainty component obtained based on the component b has a value that is the same as or greater than the certainty component at the certainty upper limit threshold value.

Aspect 15
The endoscope system according to Aspect 13 or 14, wherein
the light source apparatus is configured to emit a second light with a different wavelength band from the first light, in addition to the first light,
the imaging unit is configured to generate the first color image data and second color image data corresponding to the second light by imaging the biological tissue illuminated with the first light and the second light, and
the characteristic amount acquisition unit includes: a hemoglobin amount calculation unit configured to calculate an amount of the hemoglobin based on a first ratio of the component a and the component b; and an oxygen saturation calculation unit configured to calculate the oxygen saturation of the hemoglobin based on the amount of the hemoglobin and a second ratio between one of the component a and the component b and a component of the second color image data.

Aspect 16
The endoscope system according to Aspect 13 or 14, wherein
the first light includes three light components, and
the characteristic amount acquisition unit includes: a hemoglobin amount calculation unit configured to calculate the amount of the hemoglobin based on the first ratio obtained using the corresponding components; and an oxygen saturation calculation unit configured to calculate the oxygen saturation of the hemoglobin based on the amount of hemoglobin and a second ratio obtained using the corresponding components.

Advantageous Effects of the Disclosure

According to the above-described endoscope system of the present disclosure, information on the certainty of the oxygen saturation can be efficiently obtained and a highly-accurate oxygen saturation distribution image can be displayed.

DESCRIPTION OF EMBODIMENTS

Figure 1:
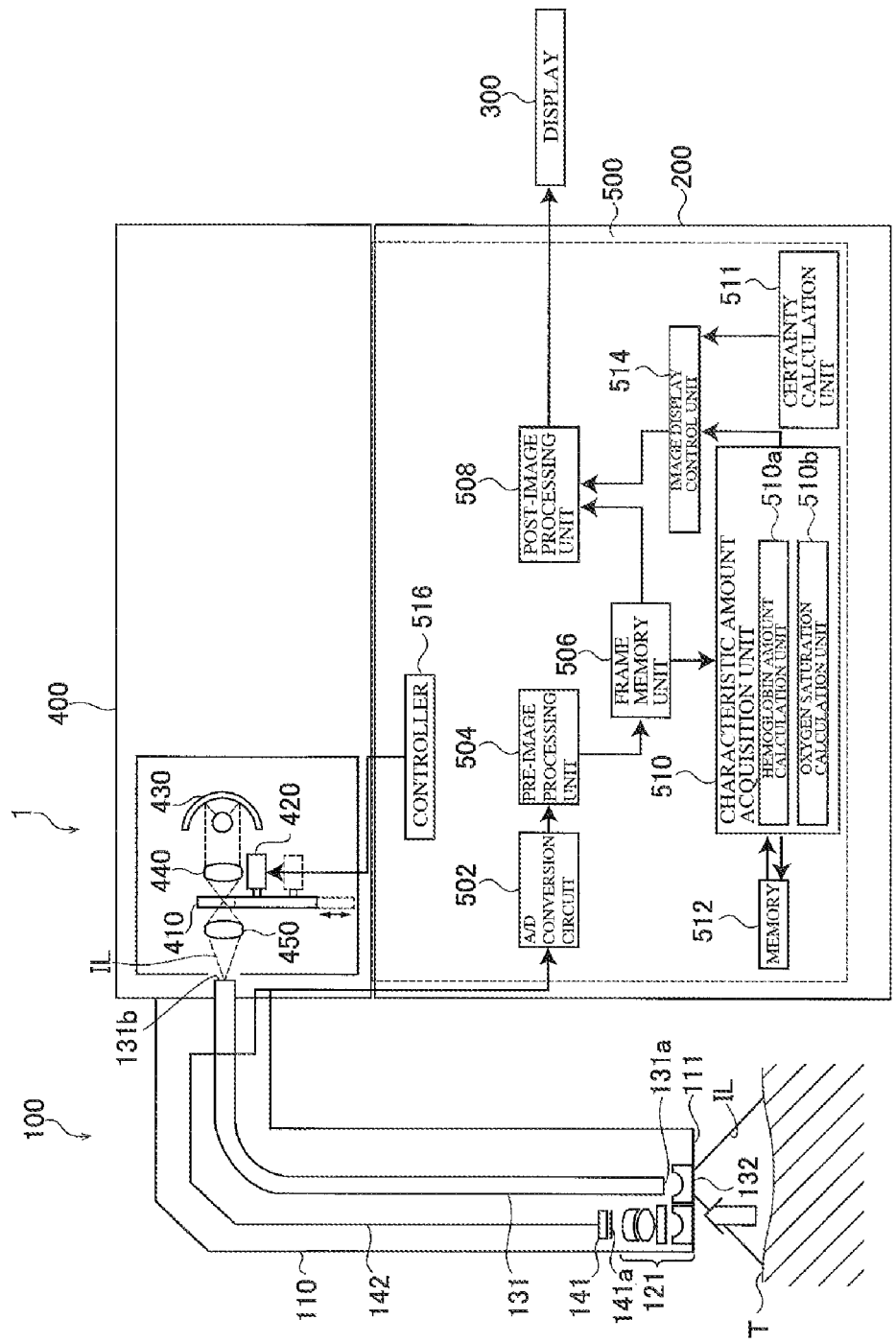
FIG. 1 is a block diagram showing a configuration of an example of an endoscope system of an embodiment.

An endoscope system of an embodiment of the present disclosure described below is a system in which an amount of hemoglobin and an oxygen saturation of biological tissue are quantitatively calculated based on multiple pieces of color image data obtained by illuminating and imaging the biological tissue as an imaging subject with light having different wavelength regions, and an oxygen saturation distribution image is displayed. However, as will be described later, there is no limitation to an embodiment in which multiple pieces of color image data are obtained by illuminating and imaging biological tissue with multiple types of light. According to another embodiment, the amount of hemoglobin and the oxygen saturation of the biological tissue can be quantitatively calculated based on one piece of color image data obtained by illuminating and imaging the biological tissue with one type of light including a light component in a desired wavelength band, and an oxygen saturation distribution image can be displayed.

With the endoscope system of an embodiment of the present disclosure, biological tissue illuminated with at least two types of light that are emitted from a light source apparatus and have different wavelength bands is imaged by an image sensor, whereby the image sensor generates color image data of the image of the biological tissue corresponding to each type of light. The processor calculates the oxygen saturation of the hemoglobin in the biological tissue using at least components a and b of the generated color image data. Furthermore, the processor calculates the certainty of the oxygen saturation using the components a and b of the color image data. According to the result of calculating the certainty, the processor controls display of the oxygen saturation distribution image, which shows a distribution of the oxygen saturation. An image display apparatus displays the controlled oxygen saturation distribution image.

Regarding the certainty, a processor sets the first value of the component a of a piece of color image data A in the color image data as a certainty lower limit threshold value at which the certainty falls below the certainty at a value greater than or equal to the first value if the value of the component a of the color image data A is lower than the first value. Furthermore, the processor sets a second value, which is greater than the first value, of the component b of a piece of color image data B in the color image data as a certainty upper limit threshold value, according to which the certainty falls below the certainty at a value that is less than or equal to the second value if the value of the component b of the color image data is greater than the second value. The processor calculates the certainty in this kind of state. The above-described color image data A and the above-described color image data B, which are used to set the certainty lower limit threshold value and the certainty upper limit threshold value, are pieces of color image data that correspond to two different types of light. Here, "certainty" means the degree to which a value can be trusted to be an original oxygen saturation value.

Specifically, in an embodiment of the present disclosure, a certainty component (the certainty component will hereinafter also be referred to as a certainty component based on color image data) included in the certainty is obtained for each value of the components a and b of the multiple pieces of color image data obtained by imaging the biological tissue illuminated with the different types of light. The certainty of the oxygen saturation is obtained by compiling the values of the certainty components based on the respective pieces of color image data into one value for each pixel. More specifically, in the embodiment, the first value of the component a of a certain piece of color image data A in the color image data is set as a lower limit threshold value of the certainty component and the second value of the component b of color image data B that is different from the color image data A is set as the upper limit threshold value of the certainty component. Similarly to the certainty lower limit threshold value, the lower limit threshold value of the certainty component is a threshold value at which the certainty component falls below the certainty component at a value that is greater than or equal to the lower limit threshold value if the value of the component a of the color image data A is lower than this value. Similarly to the certainty upper limit threshold value, the upper limit threshold value of the certainty component is a threshold value at which the certainty component falls below the certainty component at a value that is less than or equal to the upper limit threshold value if the value of the component b of the color image data B is greater than this value. Accordingly, by setting the above-described certainty component, it is possible to perform setting such that if the value of the component of the color image data A is lower than the lower limit threshold value of the component of the color image data A (under the condition that the value of the other color image data does not change), the certainty of the oxygen saturation Sat falls below the certainty of the oxygen saturation Sat at a value that is greater than or equal to the lower limit threshold value, and such that if the value of the component of the color image data B is greater than the upper limit threshold value of the component b of the color image data B (under the condition that the value of the other color image data does not change), the certainty of the oxygen saturation Sat falls below the certainty of the oxygen saturation Sat at a value that is less than or equal to the upper limit threshold value.

In this manner, the lower limit threshold value of the certainty, that is, the lower limit threshold value of the certainty of the oxygen saturation, is set based on the value of the component a of the color image data A in the color image data, and the upper limit threshold value of the certainty component, that is, the upper limit threshold value of the certainty of the oxygen saturation, is set based on the value of the component b of the color image data B, which is different from the color image data A. At this time, the upper limit threshold value of the certainty component is not determined based on the value of the component of the color image data A and the lower limit threshold value of the certainty component is not determined based on the value of the component b of the color image data.

In the calculation of the certainty in the embodiment, the certainty of the oxygen saturation is calculated based on the certainty component obtained based on the components a and b of the respective pieces of color image data. At this time, it is preferable that if the value of the component a of the color image data A is greater than the lower limit threshold value, the certainty component based on the color image data A has a value that is the same as or greater than the certainty component at the lower limit threshold value, and that if the value of the component of the color image data B is smaller than the upper limit threshold value, the certainty component b based on the color image data B has a value that is the same as or greater than the certainty component at the upper limit threshold value. In other words, the upper limit threshold value and the lower limit threshold value of the certainty component are not simultaneously determined based on values of components of the same color image data. Accordingly, the upper limit value and the lower limit value of the certainty component based on the different pieces of color image data are respectively set as the certainty lower limit threshold value and upper limit threshold value of the oxygen saturation.

Note that the method for compiling the values of the multiple certainty components into one value of certainty is not particularly limited, but in an embodiment, a method is used in which one certainty value is obtained by multiplying the determined value of the certainty component by the values of the pieces of color image data.

The color image data is data generated by illuminating biological tissue with illuminating light having different light intensities and imaging the biological tissue, and therefore if the upper limit threshold value and the lower limit threshold value of the certainty component are set for each component of one piece of color image data, the lower limit threshold value of the certainty component and the upper limit threshold value of the certainty component will be set for the component of the color image data corresponding to the illuminating light with the weak light intensity. For this reason, even if the data is suitable and reliable as the color image data, there is a possibility that the certainty of the oxygen saturation calculated using color image data having a value that exceeds the upper limit threshold value of the certainty component will be treated as being low. Furthermore, if the upper limit threshold value of the certainty component and the lower limit threshold value of the certainty component are to be set using the component of the color image data corresponding to illuminating light with a strong light intensity, even if the data is suitable and reliable as the image data, there is a possibility that the certainty of the oxygen saturation calculated using the color image data having a value that is lower than the lower limit value of the certainty component will be treated as being low. However, with an embodiment of the present disclosure, the upper limit threshold value and the lower limit threshold value of the certainty component are set based on the values of components of different pieces of color image data, and therefore the certainty of the oxygen saturation can be obtained efficiently. Also, in an embodiment of the present disclosure, parts at which the certainty of the calculated oxygen saturation is high can be displayed on an image display apparatus, and therefore a highly-accurate oxygen saturation distribution image can be displayed.

Hereinafter, an embodiment of the present disclosure will be described with reference to the drawings.

Configuration of Endoscope System

FIG. 1 is a block diagram showing a configuration of an endoscope system 1 according to an embodiment. The endoscope system 1 includes: an electronic endoscope (endoscope) 100; a processor 200; a display 300; and a light source apparatus 400. The electronic endoscope 100 and the display 300 are detachably connected to the processor 200. The processor 200 includes an image processing unit 500. The light source apparatus 400 is detachably connected to the processor 200. The light source apparatus 400 may also be incorporated in the housing of the processor 200.

The electronic endoscope 100 includes an insertion tube 110 to be inserted into the body of an examinee. A light guide 131 that extends over approximately the entire length of the insertion tube 110 is provided inside of the insertion tube 110. A leading end portion 131a, which is one end portion of the light guide 131, is located near the leading end portion of the insertion tube 110, or in other words, near an insertion tube leading end portion 111, and a base end portion 131b, which is the other end portion of the light guide 131, is located at the portion at which the light guide 131 is connected to the light source apparatus 400. Accordingly, the light guide 131 extends from the portion at which the light guide 131 is connected to the light source apparatus 400 to near the insertion tube leading end portion 111.

The light source apparatus 400 includes, as a light source, a light source lamp 430 that generates light with a large light amount, such as a xenon lamp. The light emitted from the light source apparatus 400 is incident on the base end portion 131b of the light guide 131 as illuminating light IL. The light incident on the base end portion 131b of the light guide 131 is guided through the light guide 131 to the leading end portion 131a and is emitted from the leading end portion 131a. A light distribution lens 132 that is arranged facing the leading end portion 131a of the light guide 131 is provided at the insertion tube leading end portion 111 of the electronic endoscope 100. The illuminating light IL emitted from the leading end portion 131a of the light guide 131 passes through the light distribution lens 132 and illuminates biological tissue T near the insertion tube leading end portion 111.

An object lens group 121 and an image sensor 141 are provided at the insertion tube leading end portion 111 of the electronic endoscope 100. The object lens group 121 and the image sensor 141 form an imaging unit. The light reflected or dispersed by the surface of the biological tissue T in the illuminated light IL is incident on the object lens group 121, is condensed, and forms an image on a light receiving surface of the image sensor 141. As the image sensor 141, it is possible to use a known image sensor, such as a CCD (Charge Coupled Device) image sensor or a CMOS (Complementary Metal Oxide Semiconductor) image sensor for color image imaging, with a light receiving surface provided with a color filter 141a.

Figure 2:
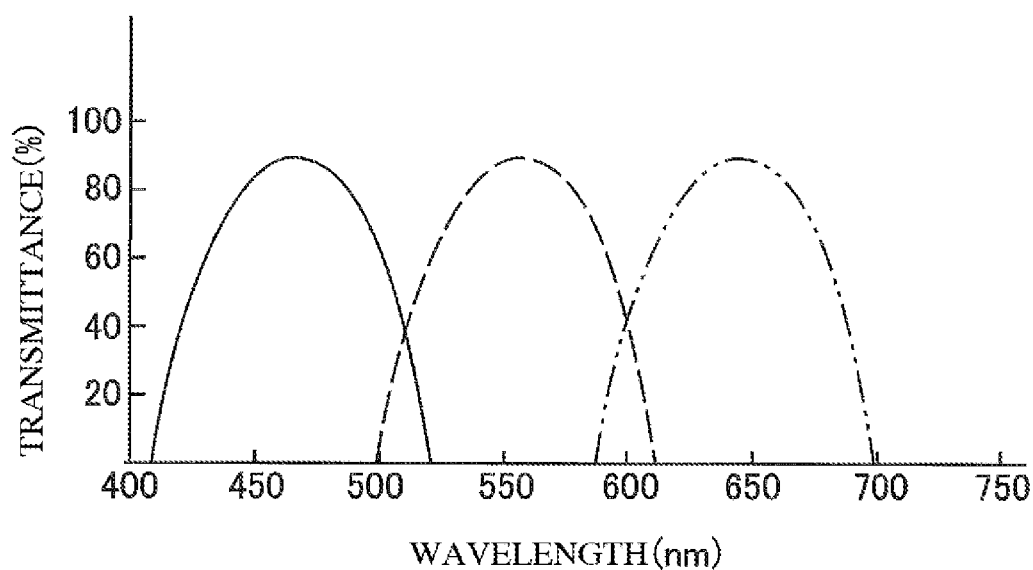
FIG. 2 is a diagram showing an example of spectral characteristics of red (R), green (G), and blue (B) filters of an image sensor used in an embodiment.

The color filter 141a is a so-called on-chip filter in which R color filters that allow transmission of red-colored light, G color filters that allow transmission of green-colored light, and B color filters that allow transmission of blue-colored light are arrayed and formed directly on the light-receiving elements of the image capture element 141. FIG. 2 is a diagram showing an example of spectral characteristics of red (R), green (G), and blue (B) filters of an image sensor used in an embodiment. The R color filter is a filter that allows transmission of light with a wavelength longer than a wavelength of about 570 nm (e.g., 580 nm to 700 nm), the G color filter is a filter that allows transmission of light with a wavelength of about 470 nm to 620 nm, and the B color filter is a filter that allows transmission of light with a wavelength shorter than a wavelength of about 530 nm (e.g., 420 nm to 520 nm).

The image sensor 141 is an imaging means for imaging the biological tissue T illuminated with the multiple types of light and generating color image data corresponding to the types of light, and is an image data generation means for generating color image data corresponding to the light reflected by or dispersed on the biological tissue T due to the biological tissue T being illuminated with multiple types of light with different wavelength ranges. The image sensor 141 is controlled so as to perform driving in synchronization with the image processing unit 500, which will be described later, and periodically (e.g., in intervals of 1/30 of a second) outputs the color image data corresponding to the image of the biological tissue T formed on the light receiving surface. The color image data output from the image sensor 141 is sent to the image processing unit 500 of the processor 200 via a cable 142.

The image processing unit 500 mainly includes: an A/D conversion circuit 502; a pre-image processing unit 504; a frame memory unit 506; a post-image processing unit 508; a characteristic amount acquisition unit 510; a certainty calculation unit 511; a memory 512; an image display control unit 514; and a controller 516.

The A/D conversion circuit 502 performs A/D conversion on the color image data input via the cable 142 from the image sensor 141 of the electronic endoscope 100 and outputs digital data. The digital data output from the A/D conversion circuit 502 is sent to the pre-image processing unit 504.

The pre-image processing unit 504 uses the digital data to generate color image data composed of R, G, and B components that form an image, or components in desired wavelength bands, through demosaic processing from R digital image data imaged by the light receiving elements in the image sensor 141 on which the R color filters are mounted, G digital image data imaged by the light receiving elements in the image sensor 141 on which the G color filters are mounted, and B digital image data imaged by the light receiving elements in the image sensor 141 on which the B color filters are mounted. Furthermore, the pre-image processing unit 504 is a portion that implements predetermined signal processing such as color correction, matrix operation, and white balance correction on the generated R, G, and B color image data.

The frame memory unit 506 temporarily stores color image data of each image that was imaged by the image sensor 141 and subjected to signal processing.

The post-image processing unit 508 generates screen data for display on a display by reading out the color image data stored in the frame memory unit 506 or performing signal processing (γ correction, etc.) on the image data generated by a later-described image display control unit 514. As will be described later, the image data generated by the image display control unit 514 includes the data of the oxygen saturation distribution image showing the distribution of the oxygen saturation of the hemoglobin in the biological tissue T. The generated image data (video format signal) is output to the display 300. Accordingly, an image of the biological tissue T, the oxygen saturation distribution image of the biological tissue T, and the like are displayed on the screen of the display 300.

As will be described later, in response to an instruction from a controller 516, the characteristic amount acquisition unit 510 calculates the amount of hemoglobin and the oxygen saturation of the hemoglobin in the imaged biological tissue T as characteristic amounts, and generates a distribution image on the image of the imaged biological tissue T, that is, a distribution image showing a distribution of the amounts of hemoglobin, and an oxygen saturation distribution image showing a distribution of the oxygen saturation of hemoglobin.

The characteristic amount acquisition unit 510 calculates the characteristic amounts by performing calculation using the color image data of the biological tissue T, and therefore the color image data and various types of information to be used by the characteristic amount acquisition unit 510 are called from the frame memory unit 506 or the memory 512.

The image display control unit 514 performs control such that the oxygen saturation distribution image of the hemoglobin generated by the characteristic amount acquisition unit 510 is overlaid on the captured image of the biological tissue T. At this time, the image display control unit 514 controls the display mode of the oxygen saturation distribution image according to the result of calculating a later-described degree of certainty.

The controller 516 is a portion that, in addition to performing operation instruction and operation control for the portions of the image processing unit 500, performs operation instruction and operation control of the portions of the electronic endoscope 100 including the light source apparatus 400 and the image sensor 141.

Note that the characteristic amount acquisition unit 510 and the image display control unit 514 may be constituted by a software module that carries out the above-described functions by starting up and executing a program in a computer, and may be constituted by hardware.

In this manner, the processor 200 includes both a function of processing the color image data output from the image sensor 141 of the electronic endoscope 100 and a function of instructing and controlling operation of the electronic endoscope 100, the light source apparatus 400, and the display 300.

According to an embodiment, the light source apparatus 400 emits at least two types of light with different wavelength regions. Specifically, the light source apparatus 400 is a light emitting means for emitting a first light, a second light, and a third light, and causes the first light, the second light, and the third light to be incident on the light guide 131. The light source apparatus 400 emits the first light, the second light, and the third light, which have different wavelength bands, but the light source apparatus 400 may also emit one or two types of light, and may also emit four or more types of light. In the case of emitting four or more types of light, the fourth light may be a light with the same wavelength band as the first light. In addition to the light source lamp 430, the light source apparatus 400 includes: a light condensing lens 440; a rotating filter 410; a filter control unit 420; and a light condensing lens 450. The light, which is approximately parallel light and is emitted from the light source lamp 430, is white light, for example, and is condensed by the light condensing lens 440, passes through the rotating filter 410, and thereafter is once again condensed by the light condensing lens 450 and is incident on the base end 131b of the light guide 131. Note that the rotating filter 410 can move between a position on the light path of the light irradiated from the light source lamp 430 to a retracted position off of the light path due to a moving mechanism (not shown), such as a linear guideway. Since the rotating filter 410 includes multiple filters with different transmission characteristics, the wavelength band of the light emitted from the light source apparatus 400 differs depending on the type of the rotating filter 410 that crosses the light path of the light irradiated from the light source lamp 430.

Note that the configuration of the light source apparatus 400 is not limited to that shown in FIG. 1. For example, a lamp that generates convergent light instead of parallel light may also be employed as the light source lamp 430. In this case, for example, a configuration may be used in which the light irradiated from the light source lamp 430 is condensed in front of the condensing lens 440 and the light is incident on the light condensing lens 440 as diffused light. Also, a configuration may be used in which the light condensing lens 440 is not used and approximately parallel light generated by the light source lamp 430 is directly incident on the rotating filter 410. Also, in the case of using a lamp that generates convergent light, a configuration may be used in which a collimator lens is used instead of the light condensing lens 440 and the light is incident on the rotating filter 410 in an approximately parallel state. For example, in the case of using an interference-type optical filter such as a multi-layered dielectric filter as the rotating filter 410, the approximately parallel light is incident on the rotating filter 410, whereby the incidence angle of the light on the optical filter is made uniform, and thus a more preferable filter characteristic can be obtained. Also, a lamp that generates diffused light may also be employed as the light source lamp 430. In this case as well, a configuration can be used in which a collimator lens is used instead of the light condensing lens 440 and the light is incident on the rotating filter 410 in an approximately parallel state.

Also, although the light source apparatus 400 is configured to emit multiple types of light with different wavelength bands by causing the light irradiated from the one light source lamp 430 to pass through the optical filter, a semiconductor light source such as a light-emitting diode or a laser element that outputs laser light, for example, can also be used as a light source apparatus 400, instead of the light source lamp 430. In this case, the rotating filter 410 need not be used. Also, for example, the light source apparatus 400 can also be configured to separately emit white light including excitation light with a predetermined wavelength band and fluorescent light that is excited to emit light by the excitation light, and light with a predetermined narrow wavelength band.

The configuration of the light source apparatus 400 is not particularly limited, as long as multiple types of light with different wavelength bands are emitted.

Although the light source apparatus 400 is an external apparatus attached to the electronic endoscope 100, if the light source apparatus 400 is constituted by a small light source such as a laser element, the light source apparatus 400 may be provided on the insertion tube leading end portion 111 of the electronic endoscope 100. In this case, the need for the light guide 131 is eliminated.

The rotating filter 410 is a circular disk-shaped optical unit including multiple optical filters, and is configured such that the transmission wavelength region is switched according to the rotation angle. The rotating filter 410 includes three optical filters with different transmission wavelength bands, but the rotating filter 410 may include four, five, six, or more optical filters. The rotation angle of the rotating filter 410 is controlled by the filter control unit 420 connected to the controller 516. Due to the controller 516 controlling the rotation angle of the rotating filter 410 via the filter control unit 420, the wavelength band of the illuminating light IL supplied to the light guide 131 is switched by passing through the rotating filter 410.

Figure 3:
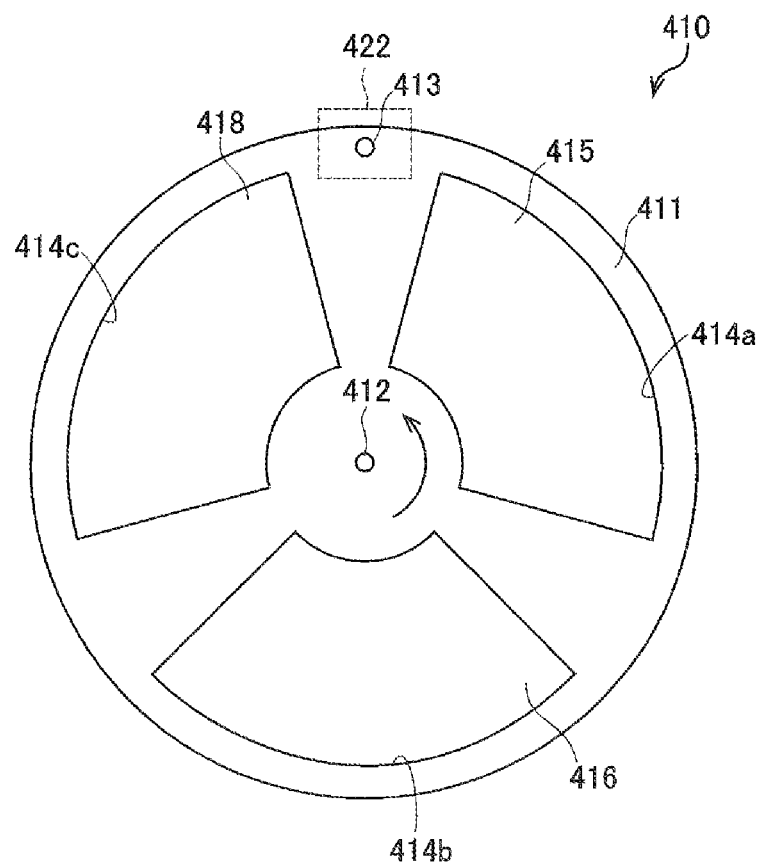
FIG. 3 is an external view (front view) of a rotating filter to be used in a light source apparatus of an embodiment.

FIG. 3 is an external view (front view) of the rotating filter 410. The rotating filter 410 includes: an approximately circular disk-shaped frame 411; and three fan-shaped optical filters 415, 416, and 418. Three fan-shaped windows 414a, 414b, and 414c are formed at an equal interval around the central axis of the frame 411, and the optical filters 415, 416, and 418 are fit into the respective windows 414a, 414b, and 414c. Note that the optical filters are all multilayered dielectric filters, but another type of optical filter (e.g., an absorption-type optical filter or an etalon filter in which a dielectric multilayer film is used as a reflection film, etc.) may also be used.

Also, a boss hole 412 is formed on the central axis of the frame 411. An output shaft of a servo motor (not shown) included in the filter control unit 420 is fixed by being inserted into the boss hole 412 and the rotating filter 410 rotates along with the output shaft of the servo motor.

When the rotating filter 410 rotates in the direction indicated by the arrow in FIG. 3, the optical filters on which the light is incident switch in the following order: optical filters 415, 416, and 418, and thereby the wavelength bands of the illuminating light IL passing through the rotating filter are sequentially switched.

Figure 4:
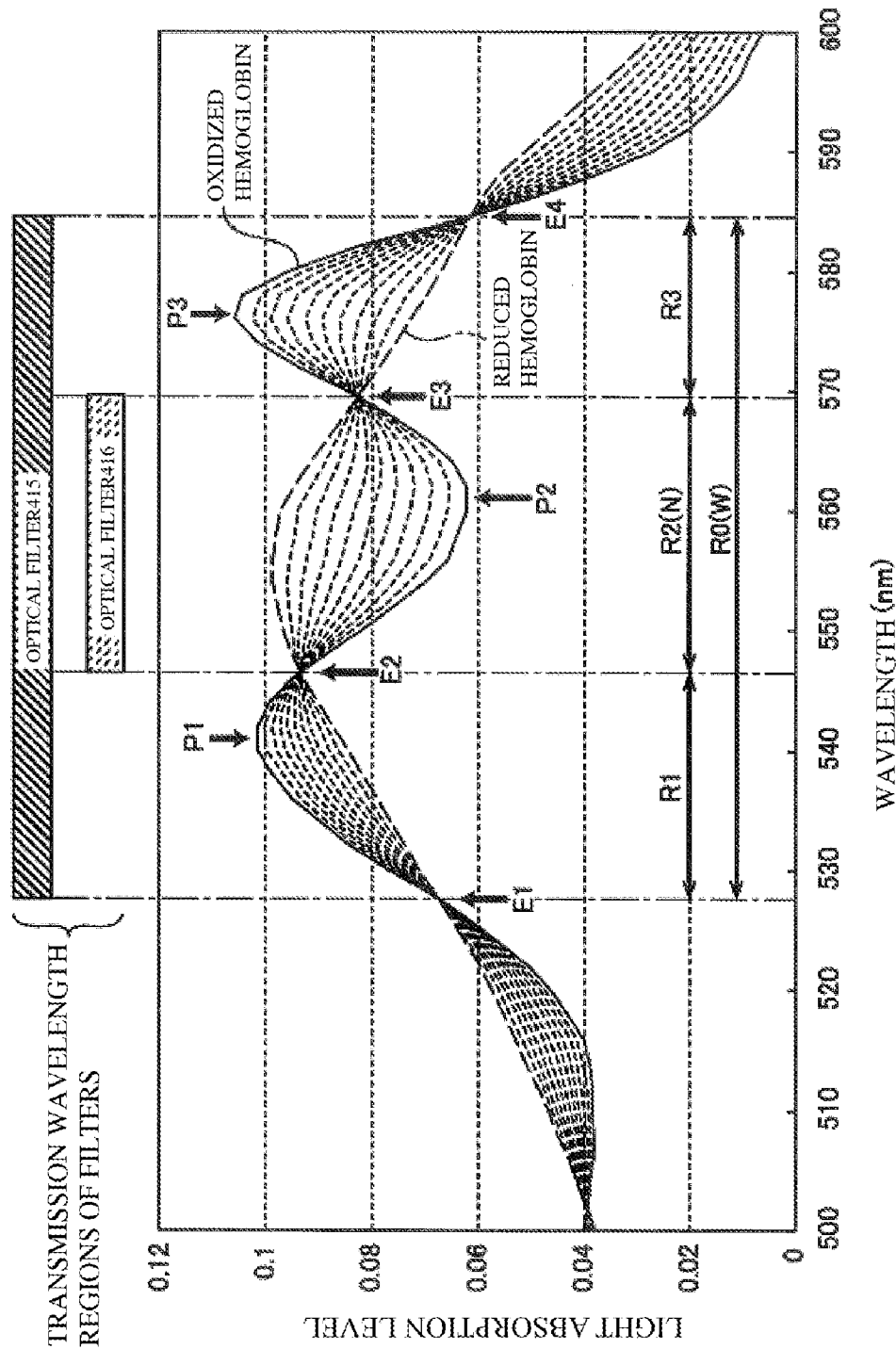
FIG. 4 is a diagram showing an example of an absorption spectrum of hemoglobin near 550 nm.

The optical filters 415 and 416 are optical band-pass filters that selectively allow transmission of light in the 550-nm band. As shown in FIG. 4, the optical filter 415 is configured to allow transmission with low loss of light in a wavelength band R0 (W band) from the isosbestic points E1 to E4, and to block light of other wavelength regions. Also, the optical filter 416 is configured to allow transmission with low loss of light in the wavelength band R2 (N band) from the isosbestic point E2 to the isosbestic point E3, and to block light of other wavelength regions.

Also, the optical filter 418 is an ultraviolet-cutting filter, and in the visible light wavelength region, the light emitted from the light source lamp 430 passes through the optical filter 418. The light that has passed through the optical filter 418 is used as white light WL to capture a normal observation image. Note that it is also possible to use a configuration in which the optical filter 418 is not used and the window 414c of the frame 411 is open.

Accordingly, the light that has passed through the optical filter 415 among the light irradiated from the light source lamp 430 is referred to hereinafter as "wide light", the light that has passed through the optical filter 416 among the light irradiated from the light source lamp 430 is referred to hereinafter as "narrow light", and light that has passed through the optical filter 418 among the light irradiated from the light source lamp 430 is referred to hereinafter as "white light WL".

As shown in FIG. 4, the wavelength band R1 is a band in which the peak wavelength of an absorption peak P1 originating from oxidized hemoglobin is included, the wavelength band R2 is a band in which the peak wavelength of an absorption peak P2 originating from reduced hemoglobin is included, and the wavelength band R3 is a band in which the peak wavelength of an absorption peak P3 originating from oxidized hemoglobin is included. Also, the peak wavelengths of the three absorption peaks P1, P2, and P3 are included in the wavelength region R0. Note that FIG. 4 is a diagram showing an example of an absorption spectrum of hemoglobin near 550 nm.

Also, the wavelength band R0 of the optical filter 415 and the wavelength band R2 of the optical filter 416 are included in the transmission wavelength region (FIG. 2) of the G color filter of the color filter 141a. Accordingly, images of the biological tissue T formed by light that has passed through the optical filters 415 and 416 are obtained as images of the G component of the color image data captured by the image sensor 141.

A through hole 413 is formed on the circumferential edge portion of the frame 411. The through hole 413 is formed at the same position (phase) as the boundary portion between the window 414a and the window 414c in the rotation direction of the frame 411. A photointerrupter 422 for detecting the through hole 413 is arranged on the periphery of the frame 411 so as to surround part of the circumferential edge portion of the frame 411. The photointerrupter 422 is connected to the filter control unit 420.

Thus, it is preferable to have a configuration in which the light source apparatus 400 emits types of light with different wavelength bands, that is, the wide light, the narrow light, and the white light WL, as the illuminating light IL by sequentially switching the multiple optical filters 415, 416, and 418 on the light path of the light irradiated by the light source lamp 430.

Calculation of Characteristic Amount of Biological Tissue

A characteristic amount of the biological tissue T is calculated by the characteristic amount acquisition unit 510 of the processor 500. Processing for calculating the amount of hemoglobin and the oxygen saturation Sat of the hemoglobin in the biological tissue T as the characteristic amounts from a captured image of the biological tissue T will be described below.

As shown in FIG. 4, hemoglobin has strong absorption bands called Q bands, which originate from porphyrin, near 550 nm. The absorption spectrum of hemoglobin changes according to the oxygen saturation Sat, which indicates the percentage of oxidized hemoglobin HbO in all of the hemoglobin. The waveform with the solid line in FIG. 4 is the absorption spectrum of an oxygen saturation Sat of 100%, that is, oxidized hemoglobin, and the waveform with the long broken line is the absorption spectrum of an oxygen saturation Sat of 0%, that is, reduced hemoglobin Hb. Also, the short broken lines are the absorption spectra of hemoglobin with intermediate oxygen saturations Sat of 10%, 20%, 30%, . . . and 90%, that is, a mixture of oxidized hemoglobin HbO and reduced hemoglobin Hb.

As shown in FIG. 4, in the Q band, the oxidized hemoglobin HbO and the reduced hemoglobin Hb have mutually different peak wavelengths. Specifically, the oxidized hemoglobin HbO has an absorption peak P1 near the wavelength 542 nm and an absorption peak P3 near the wavelength 576 nm. On the other hand, the reduced hemoglobin Hb has an absorption peak P2 near 556 nm. Since FIG. 4 shows absorption spectra in the case where the sum of the concentrations of the oxidized hemoglobin HbO and the reduced hemoglobin Hb is constant, isosbestic points E1, E2, E3, and E4, at which the light absorption degree is constant regardless of the proportion of the oxidized hemoglobin HbO and the reduced hemoglobin Hb, that is, regardless of the oxygen saturation, appear. In the following description, the wavelength band interposed between the isosbestic points E1 and E2 is the wavelength band R1, which was described above for the optical filter 410, the wavelength band interposed between the isosbestic points E2 and E3 is the wavelength band R2, the wavelength band interposed between the isosbestic points E3 and E4 is the wavelength band R3, and the wavelength band interposed between the isosbestic points E1 and E4, that is, the band obtained by combining the wavelength bands R1, R2, and R3, is the wavelength band R0. Accordingly, the wavelength band of the wide light, which is the transmission light that passed through the optical filter 415 among the light irradiated from the light source lamp 430, is the wavelength band R0, and the wavelength band of the narrow light, which is the transmission light that passed through the optical filter 416 among the light irradiated from the light source lamp 430, is the wavelength band R2.

As shown in FIG. 4, in the wavelength bands R1, R2, and R3, the absorption of the hemoglobin increases or decreases linearly with respect to the oxygen saturation. Specifically, absorptions AR1 and AR3 of the hemoglobin in the wavelength bands R1 and R3 linearly increase with respect to the concentration of the oxidized hemoglobin, that is, the oxygen saturation. Also, the absorption AR2 of the hemoglobin in the wavelength band R2 increases linearly with respect to the concentration of the reduced hemoglobin.

Here, the oxygen saturation is defined using the following equation (1).

Equation (1):

$$Sat = \frac{[HbO]}{[Hb] + [HbO]} \quad \text{Equation 1}$$

where
Sat: oxygen saturation
[Hb]: Concentration of reduced hemoglobin
[HbO]: Concentration of oxidized hemoglobin
[Hb]+[HbO]: Amount of hemoglobin (tHb)

Also, equation (2) and equation (3), which indicate the concentrations of the oxidized hemoglobin HbO and the reduced hemoglobin Hb, are obtained using equation (1).

Equation (2):

$$[HbO] = Sat \cdot ([Hb] + [HbO]) \quad \text{Equation 2}$$

Equation (3):

$$[Hb] = (1 - Sat) \cdot ([Hb] + [HbO]) \quad \text{Equation 3}$$

Accordingly, the absorptions AR1, AR2, and AR3 of the hemoglobin are characteristic amounts that depend on both the oxygen saturation and the amount of hemoglobin.

Here, it is evident that the total value of the light absorption level in the wavelength band R0 is a value that does not depend on the oxygen saturation Sat and is determined by the amount of hemoglobin. Accordingly, the amount of hemoglobin can be quantified based on the total value of the light absorption level in the wavelength band R0. Also, the oxygen saturation Sat can be quantified based on the total value of the light absorption levels in the wavelength band R1, the wavelength band R2, or the wavelength band R3, and the amount of hemoglobin quantified based on the total value of the wavelength band R0.

The characteristic amount acquisition unit 510 includes: a hemoglobin amount calculation unit 510a that calculates and acquires the amount of hemoglobin in the biological tissue T based on a later-described first ratio that is sensitive to change in the amount of hemoglobin in the biological tissue T; and an oxygen saturation calculation unit 510b that calculates and acquires the oxygen saturation of the hemoglobin in the biological tissue T based on the calculated amount of hemoglobin and a later-described second ratio that is sensitive to change in the oxygen saturation of the hemoglobin. The first ratio and the second ratio being sensitive to change in the amount of the hemoglobin or change in the oxygen saturation means that the first ratio and the second ratio change with respect to change in the amount of hemoglobin or change in the oxygen saturation.

Due to the fact that the value of the luminance component of the color image data of the biological tissue T illuminated with the wide light (the light in the wavelength band R0 that passed through the optical filter 415) corresponds to the total value of the light absorption levels in the above-described wavelength band R0, the hemoglobin amount calculation unit 510a of the characteristic amount acquisition unit 510 calculates the amount of hemoglobin based on the luminance component of the color image data in the wavelength band R0. Here, the luminance component can be calculated by multiplying a predetermined coefficient by the R component of the color image data, multiplying a predetermined coefficient by the G component of the color image data, multiplying a predetermined coefficient by the value of the B component of the color image data, and adding together the multiplication results.

Specifically, the hemoglobin amount calculation unit 510a of the characteristic amount acquisition unit 510 calculates the amount of hemoglobin based on a ratio Wide(Yh)/WL(R) or Wide(Yh)/{WL(R)+WL(G)} (first ratio) obtained by dividing the luminance component Wide (Yh) of the color image data (second color image data) of the biological tissue T in which the wide light (second light) is used as the illuminating light IL, by an R component WL(R) or a total component WL(R)+WL(G) of the R component WL(R) and a G component WL(G) of the color image data (first color image data) of the biological tissue T in which the white light WL (first light) is used as the illuminating light IL. The ratio Wide(Yh)/WL(R) or Wide(Yh)/{WL(R)+WL(G)} obtained by dividing the luminance component Wide(Yh) by WL(R) or {WL(R)+WL(G)} is used in the calculation of the amount of hemoglobin in order to cancel out changes in the spectral characteristic of the biological tissue T according to the degree to which the illuminating light IL is diffused by the surface of the biological tissue T. In particular, the reflection spectrum of biological tissue T of the inner wall of a digestive organ or the like is easily influenced by the wavelength property of the diffusion of the illuminating light by the biological tissue T, in addition to the wavelength property (specifically, the absorption spectrum property of the oxidized hemoglobin and the reduced hemoglobin) of the absorption by the components constituting the biological tissue T. The R component WL(R) or the total component WL(R)+WL(G) of the R component and the G component of the color image data (first color image data) of the biological tissue T in which the white light WL (first light) is used as the illuminating light IL is not influenced by the amount of hemoglobin and the oxygen saturation Sat and indicates the degree of diffusion of the biological tissue T of the illuminating light IL. Accordingly, in order to cancel out the influence of the diffusion of the biological tissue T of the illuminating light IL from the reflection spectrum of the biological tissue T, the wavelength band of the white light WL (reference light) is preferably set such that one component of the color image data includes a wavelength band that is not sensitive to change in the amount of hemoglobin in the biological tissue T. In addition to this, the wavelength band of the white light WL (reference light) is preferably set such that one component of the color image data includes a wavelength band that is not sensitive to change in the oxygen saturation.

According to an embodiment, a reference table, which indicates the correlation between information of the above-described first ratio and the amount of hemoglobin in the biological tissue with a known amount of hemoglobin, is stored in the memory 512 in advance, and the hemoglobin amount calculation unit 510a of the characteristic amount acquisition unit 510 uses the reference table to calculate the amount of hemoglobin based on the above-described first ratio in the color image data obtained by imaging the biological tissue T.

In the calculation of the amount of hemoglobin of an embodiment, it is preferable to use, as the first ratio, a ratio Wide(Yh)/WL(R) or Wide(Yh)/{WL(R)+WL(G)} of the luminance component Wide(Yh) of the color image data (second color image data) of the biological tissue T in which the wide light (second light) is used as the illuminating light IL and the R component WL(R) or the total components WL(R)+WL(G) of the R component and the G component of the color image data (first color image data) of the biological tissue T in which the white light WL (first light) is used as the illuminating light IL, but it is also preferable to use the G component Wide(G) instead of the luminance component Wide(Yh) of the color image data (second color image data) of the biological tissue T in which the wide light (second light) is used as the illuminating light IL.

Furthermore, as described above, due to the fact that the total value of the light absorption level in the wavelength band R2 decreases along with an increase in the oxygen saturation Sat, and that the total value of the light absorption level in the wavelength band R0 changes according to the amount of hemoglobin but is constant regardless of changes in the oxygen saturation Sat, the oxygen saturation calculation unit 510b of the characteristic amount acquisition unit 510 calculates the oxygen saturation based on the second ratio determined below. That is, the oxygen saturation calculation unit 510b of the characteristic amount acquisition unit 510 calculates, as the second ratio, a ratio Narrow(Yh)/Wide(Yh) of the luminance component Narrow(Yh) of the color image data (third color image data) of the biological tissue T illuminated with the narrow light, which is the light in the wavelength band R2 that passed through the optical filter 416, and the luminance component Wide(Yh) of the color image data (second color image data) of the biological tissue T illuminated with the wide light (the light in the wavelength band R0 that passed through the optical filter 416). On the other hand, a correlation indicating the relationship between the amount of hemoglobin, the lower limit value of the second ratio at which the oxygen saturation Sat=0%, and the upper limit value of the second ratio Narrow(Yh)/Wide(Yh) at which the oxygen saturation Sat=100% is obtained from a known sample and stored in advance in the memory 512. The oxygen saturation calculation unit 510b of the characteristic amount acquisition unit 510 obtains the lower limit value and the upper limit value of the second ratio using the above-described correlation and the calculation result of the amount of hemoglobin obtained from the color image data generated by imaging the biological tissue T. Furthermore, the oxygen saturation calculation unit 510b calculates the position in the range between the upper limit value and the lower limit value in which the value of the second ratio Narrow(Yh)/Wide(Yh) of the imaged biological tissue T is located, using the fact that the oxygen saturation Sat changes linearly according to the second ratio between the obtained lower limit value and upper limit value. In this manner, the oxygen saturation calculation unit 510b of the characteristic amount acquisition unit 510 calculates the oxygen saturation Sat.

Also, according to an embodiment, a reference table indicating the amount of hemoglobin and the correlation between the value of the second ratio and the oxygen saturation Sat of the hemoglobin is obtained from a known sample and stored in advance in the memory 512, and the oxygen saturation Sat of the hemoglobin can also be calculated based on the calculated second ratio by referencing the reference table.

In one embodiment, the second ratio is used as a ratio between the luminance component Narrow(Yh) of the color image data (third color image data) of the biological tissue T illuminated with the narrow light and the luminance component Wide(Yh) of the color image data (second color image data) of the biological tissue T illuminated with the wide light, but it is also possible to use the ratio between the G component Narrow(G) of the color image data (third color image data) of the biological tissue T illuminated with the narrow light and the G component Wide(G) of the color image data (second color image data) of the biological tissue T illuminated with the wide light.

Also, in the above-described embodiment, in order to calculate the second ratio, the narrow light in the wavelength band R2 is used to illuminate the biological tissue T, but there is no limitation to the narrow light. For example, it is also possible to use light whose wavelength band is the wavelength band R1 or the wavelength band R2, with the intention of using the wavelength band R1 or the wavelength band R2 in which the total value of the light absorption level changes with respect to change in the oxygen saturation Sat.

In this case, the filter characteristic of the optical filter 416 is preferably set to the wavelength band R1 or the wavelength band R2.

Thus, according to an embodiment, it is preferable that the wavelength band of the narrow light (third light) is included in the wavelength band of the wide light (second light) in order to accurately calculate the oxygen saturation Sat. Also, in light of the fact that the oxygen saturation Sat can be calculated accurately, the wavelength band of the wide light (second light) is preferably set such that one component of the second color image data, such as the luminance component or G component, includes the wavelength band R0, which is sensitive to change in the amount of hemoglobin but is not sensitive to change in the oxygen saturation. In light of the fact that the oxygen saturation Sat can be calculated accurately, the wavelength band of the narrow light (third light) is set such that one component of the third color data, such as the luminance component or the G component, includes the wavelength band R2, which is sensitive to change in the oxygen saturation Sat of the biological tissue T.

Also, in light of the fact that the influence of the spectral property of the diffused light on the biological tissue T can be canceled out, the wavelength band of the white light WL (first light) is preferably set such that one component of the first color image data includes a wavelength band that is not sensitive to change in the amount of hemoglobin of the biological tissue T.

Also, it is preferable that the above-described wide light (second light) is filtered white light WL (first light) obtained by allowing the first wavelength band in the region from 500 nm to 600 nm, for example, the wavelength band between the isosbestic point E1 and the isosbestic point E4, in the wavelength band of the white light WL (first light) to pass through one optical filter, and the narrow light (third light) is filtered light of the white light WL (first light) obtained by allowing a second wavelength band that is narrower than the first wavelength band in the range of the first wavelength band, such as the wavelength band between the isosbestic point E2 and the isosbestic point E3, to pass through one optical filter. For example, the first wavelength band is preferably a band in the range of 510 nm to 590 nm. Also, for example, the second wavelength band is preferably a band in the region of 510 nm to 590 nm, and is more preferably a band in the region of 530 nm to 580 nm.

Also, in the above-described embodiment, when the light absorption level of the hemoglobin is used to calculate the hemoglobin amount and the oxygen saturation, the light in the wavelength band near 550 nm is used as illuminating light, but this is an example. In the light absorption level of the hemoglobin, outside of the wavelength band near 550 nm, a large absorption peak exists at 420 to 450 nm and includes isosbestic points. In the periphery of the isosbestic points, the waveforms of the absorption spectra of the oxidized hemoglobin and the reduced hemoglobin are alternatingly switched. For this reason, in an embodiment, it is also preferable that the hemoglobin amount and the oxygen saturation are calculated using light with different wavelengths or wavelength bands in the wavelength band of 400 to 460 nm as the illuminating light.

Figure 5:
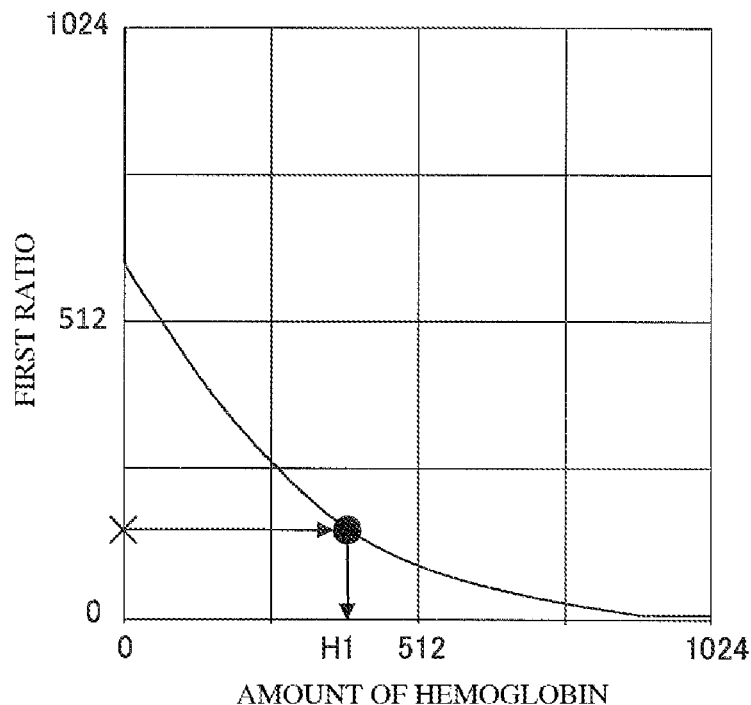
FIG. 5 is a diagram showing an example of a relationship between a first ratio and an amount of hemoglobin, which is used in an embodiment.

FIG. 5 is a diagram showing an example of a relationship between a first ratio and an amount of hemoglobin. When the first ratio is obtained as described above, the hemoglobin amount calculation unit 510*a* of the characteristic amount acquisition unit 510 references the reference table showing the relationship shown in FIG. 5 and obtains the amount of hemoglobin based on the obtained first ratio. FIG. 5 indicates that the hemoglobin amount H1 is obtained based on the value of the first ratio. The numerical values on the horizontal axis and the vertical axis of FIG. 5 are denoted as the values 0 to 1024 for convenience.

Figure 6:
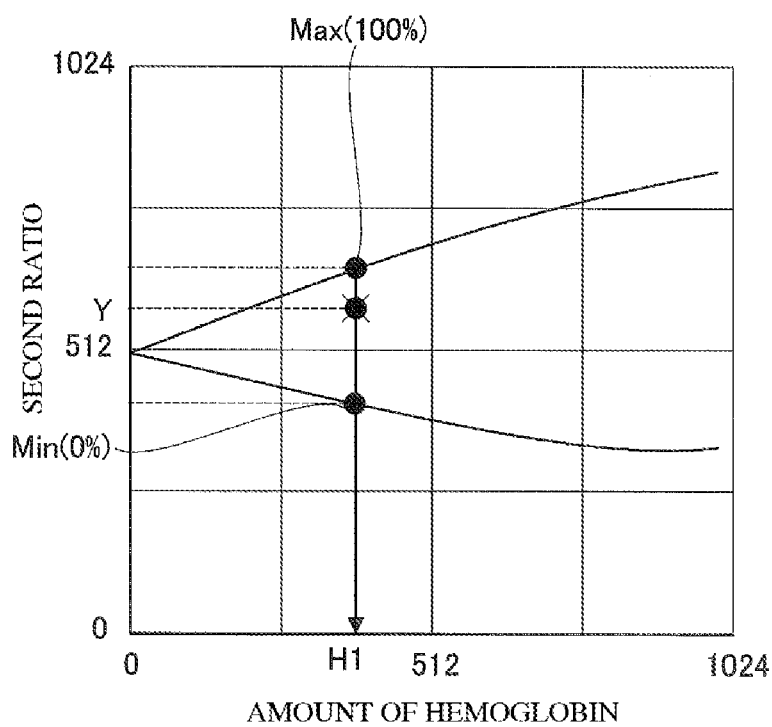
FIG. 6 is a diagram showing an example of a relationship between an upper limit value and a lower limit value of a second ratio and an amount of hemoglobin, which is used in an embodiment.

FIG. 6 is a diagram showing an example of a relationship between the upper limit value and lower limit value of the second ratio and the amount of hemoglobin. The numerical values on the horizontal axis and the vertical axis of FIG. 6 are denoted as the values 0 to 1024 for convenience.

When the second ratio is obtained as described above, the oxygen saturation amount calculation unit 510*b* of the characteristic amount acquisition unit 510 uses the correlation shown in FIG. 6 to obtain the upper limit value and the lower limit value of the second ratio in the obtained amount of hemoglobin, based on the second ratio and the amount of hemoglobin obtained by the hemoglobin amount calculation unit 510*a*. The upper limit value indicates that the oxygen saturation Sat=100%, and the lower limit value indicates that the oxygen saturation Sat=0%. By determining the position between the upper limit value and the lower limit value at which the obtained second ratio is located, the oxygen saturation amount calculation unit 510*b* obtains the value of the oxygen saturation Sat. In FIG. 6, the value of the second ratio is Y. In FIG. 6, the upper limit value Max (100%) and the lower limit value Min (0%) when the value of the hemoglobin is H1 is obtained. The value of the oxygen saturation Sat is obtained based on the upper limit value Max (100%), the lower limit value Min (0%), and the value Y of the second ratio.

The oxygen saturation Sat obtained in this manner is obtained for each pixel of the image of the biological tissue T, and therefore the distribution of the oxygen saturation Sat on the image of the biological tissue T can be shown as an oxygen saturation distribution image. The oxygen saturation distribution image is indicated by a gradation in which the color of the pixels is changed (e.g., changed from red to blue) according to the values of the oxygen saturation Sat of the pixels. For example, the oxygen saturation distribution image includes a distribution image in which only the pixels located in the range of the above-described oxygen saturations are indicated by the gradation in a region of a part of the image of the biological tissue T.

Calculation of Certainty of Oxygen Saturation

As described above, in the endoscope system 1, the oxygen saturation Sat of the hemoglobin is calculated using the first ratio and second ratio obtained based on a component of the color image data corresponding to the types of light, which is generated by the biological tissue T being illuminated with the light and being imaged, and therefore even if the value of the oxygen saturation Sat is not an abnormal value, the value of the component of the color image data used in the calculation of the first ratio and second ratio is very large in some cases and very small in some cases. For example, if the value of the component of the color image data is very large, there is a possibility that the value is the output of a region in which the output characteristic for the received light amount of the image sensor 141 is close to being non-linear. Also, if the value of the color image data is very small, the SN ratio (signal to noise ratio) becomes smaller, and therefore even if the calculated value of the oxygen saturation Sat is not an abnormal value, there is a possibility that the value will be shifted from the original oxygen saturation. In the embodiment, the likelihood of a shift from the original oxygen saturation is indicated as the certainty. That is, it is indicated that the higher the certainty is, the lower the likelihood of a shift from the original oxygen saturation is, and the higher the degree to which the value of the oxygen saturation can be trusted is.

The image processing unit 500 includes a certainty calculation unit 511 for calculating the above-described certainty. When the certainty calculation unit 511 is connected to the characteristic amount calculation unit 510 and calculates the oxygen saturation Sat, the certainty calculation unit 511 calculates a certainty component included in the certainty of the oxygen saturation Sat for each pixel using the pieces of color image data used to calculate the first ratio and the second ratio, and furthermore calculates the certainty of the oxygen saturation Sat based on the certainty component. In an embodiment, the certainty is a product obtained by multiplying the certainty components. The certainty calculation unit 511 sends the calculated certainty to the image display control unit 514. In an embodiment, the certainty and the certainty component are indicated by values in a range of 0 to 1, and the greater the value is, the higher the certainty is.

The certainty calculation unit 511 may be constituted by a software module that carries out a function described below by starting up and executing a program on the computer along with the characteristic amount acquisition unit 510 and the image display control unit 514, or may be constituted by hardware.

Figure 7:
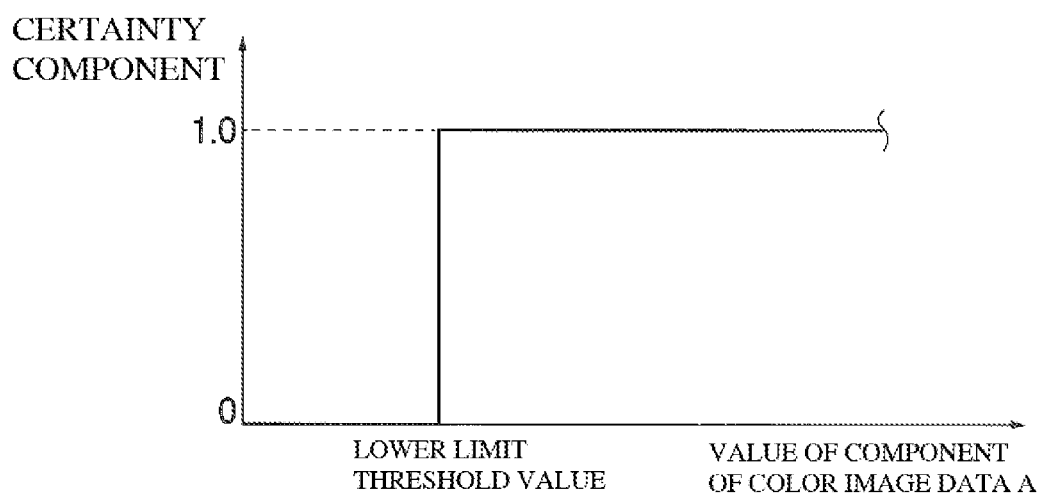
FIG. 7 is a diagram illustrating an example of a certainty component determined by a certainty calculation unit of an embodiment.
Figure 8:
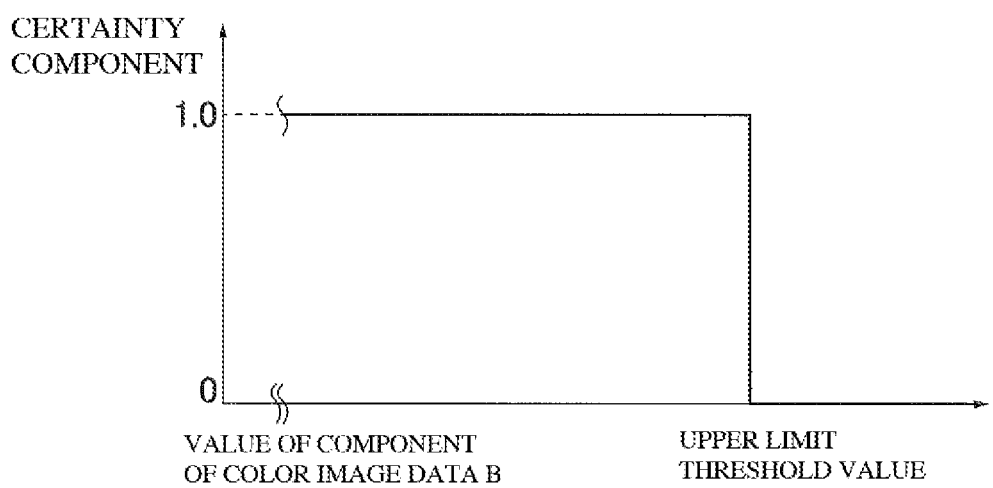
FIG. 8 is a diagram illustrating an example of a certainty component determined by a certainty calculation unit of an embodiment.

FIGS. 7 and 8 are diagrams for illustrating examples of certainty components that constitute the certainty determined by the certainty calculation unit 511 of an embodiment. Specifically, the certainty component unit 511 determines the certainty component in a state in which a first value of a component a of color image data A is set as the lower limit threshold value at which the certainty component falls below the certainty component at a value greater than or equal to the first value (in FIG. 7, decreases from a constant value) if the value of the component a of the color image data is lower than the first value.

Furthermore, the certainty calculation unit 511 determines the certainty component in a state in which a second value of a component b of color image data B, which is greater than the first value, is set as an upper limit threshold value at which the certainty component falls below the certainty component at a value less than or equal to the second value (in FIG. 8, falls below a certain value) if the value of the component b of the color image data is greater than the second value. At this time, the lower limit threshold value of the certainty component and the upper limit threshold value of the certainty component are values of components in the color image data corresponding to two different types of light. Note that the components of the color image data include values that are all dispersed in the same numerical value range, and for example, integer values are set to the components within ranges such as 0 to 255, 0 to 1023, or 0 to 4095.

In the example shown in FIG. 7, if the value of the component a of the color image data A is greater than the lower limit threshold value, the certainty component is the same value as that of the certainty component at the lower limit value, and in the example shown in FIG. 8, if the value of the component b of the color image data B is smaller than the upper limit threshold value, the certainty component is set to be the same as that of the certainty component at the upper limit threshold value. However, it is also possible to enter a state in which if the value of the component of the color image data A is greater than the lower limit threshold value, the certainty component has a value greater than the certainty component at the lower limit threshold value, and if the value of the component of the color image data B is smaller than the upper limit threshold value, the certainty component is set so as to have a value greater than the certainty component at the upper limit threshold value. That is, the upper limit threshold value of the certainty component is not set based on the color image data A and the lower limit threshold value of the certainty component is not set based on the color image data B.

Thus, in the embodiment, if the value of the component a of the color image data A is lower than the lower limit threshold value of the component of the color image data A due to the threshold value being determined (under the condition that the value of the other color image data does not change), the certainty of the oxygen saturation Sat becomes lower than the certainty of the oxygen saturation Sat at a value greater than or equal to the lower limit threshold value, and if the value of the component b of the color image data B is higher than the upper limit threshold value of the component b of the color image data B (under the condition that the value of the other color image data does not change), the certainty of the oxygen saturation Sat can be set such that it does not fall below the certainty of the oxygen saturation Sat at a value less than or equal to the upper limit threshold value.

As described above, the color image data used to calculate the oxygen saturation Sat includes the first color image data of the biological tissue T illuminated with the white light WL, the second color image data of the biological tissue T illuminated with the wide light, and the third color image data of the biological tissue T illuminated with the narrow light.

The certainty calculation unit 511 preferably uses the value of a component of the third color image data, for example, the value of the luminance component, as the lower limit threshold value of the certainty component. The certainty calculation unit 511 preferably uses the value of the component of the first color image data or the value of the component of the second color image data, for example, the value of the luminance component, as the upper limit threshold value of the certainty component. That is, it is preferable that the third color image data is used as the color image data A and the first color image data or the second color image data is used as the color image data B.

The third color image data is data that is obtained by illuminating the biological tissue T with narrow light, the narrow light is filtered light generated by passing the light irradiated from the light source lamp 430 through the optical filter 416, and since the wavelength band of the narrow light is narrower than those of the white light WL or the wide light, the light intensity of the narrow light tends to be lower than the light intensity of the white light WL and the wide light. For this reason, the value of the component of the third color image data is smaller than the value of the component of the first color image data and the value of the component of the second color image data. For this reason, regarding the third color image data, which tends to have a small value, the certainty calculation unit 511 sets the certainty calculated using a small value outside of the allowed range to be low, in consideration of the SN ratio and the like. On the other hand, the value of the component of the first color image data or the second color image data tends to have a wide transmission wavelength band of light in the optical filter and tends to be greater than the value of the component of the third color image data. For this reason, regarding the first color image data or the second color image data, which tends to have a large value, the certainty calculation unit 511 sets the certainty of the oxygen saturation Sat calculated using a large value outside of the allowed range to be low considering the output property or the like of the image sensor 141. Thus, according to an embodiment, as shown in FIG. 7, the color image data A for setting the lower limit threshold value is preferably color image data obtained using light that has the weakest light intensity among the multiple types of light to be used as the illuminating light. Also, according to an embodiment, the color image data B for setting the upper limit threshold value to the value of the component of the color image data as shown in FIG. 8 preferably includes the color image data obtained using the light with the strongest light intensity among the multiple types of light to be used as the illuminating light.

Accordingly, the lower limit threshold value of the certainty component is set using the third color image data, but the upper limit threshold value is not, and the upper limit threshold value of the certainty component is set using the first color image data and the second color image data, but the lower limit threshold value is not.

The certainty calculation unit 511 may also set the upper limit threshold value of the certainty component with respect to the first color image data and the second color image data, and may also set the upper limit threshold value of the certainty component with respect to one of the first color image data and the second color image data. In the case where the upper limit threshold value of the certainty component is set with respect to each of the first color image data and the second color image data, the upper limit threshold values may be the same, but they are preferably different.

The certainty component based on this kind of color image data is obtained for each component of at least two pieces of color image data, and for each pixel, and therefore the certainty calculation unit 511 multiplies the values of the certainty components of the corresponding pixels of the at least two pieces of color image data in order to consolidate it as the certainty of one oxygen saturation Sat. The certainty calculation unit 511 uses the value of each pixel obtained through multiplication as the value of the certainty of the oxygen saturation Sat.

The certainty calculation unit 511 sends the calculated value of the certainty of each pixel to the pixel image display control unit 514.

Figure 9:
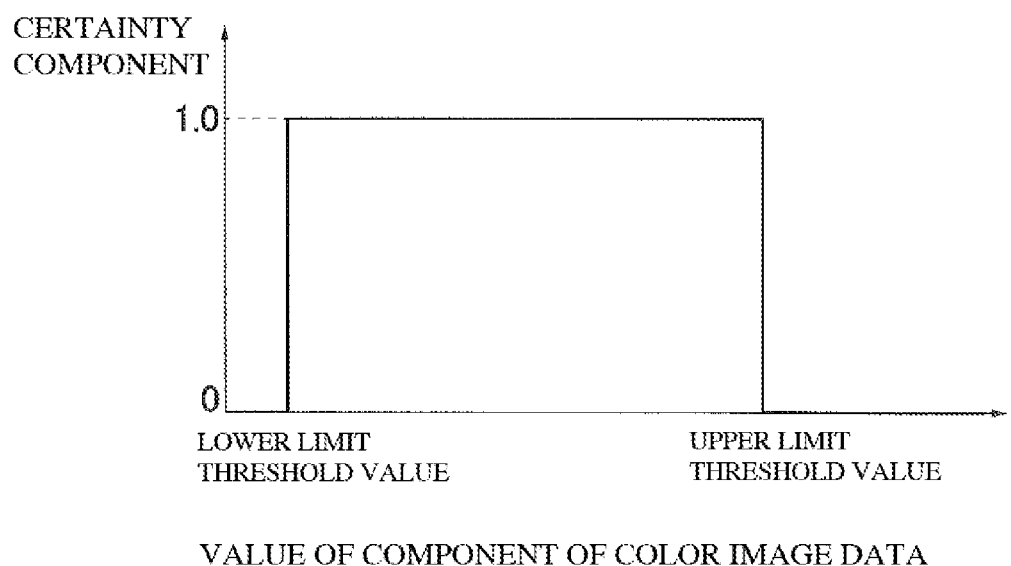
FIG. 9 is a diagram illustrating an example in which a lower limit threshold value and an upper limit threshold value of the certainty component are set with respect to one piece of color image data.

FIG. 9 is a diagram illustrating an example in which a lower limit threshold and an upper limit threshold of the certainty component are set with respect to one piece of color image data. As shown in FIG. 9, if the lower limit threshold value and the upper limit threshold value of the certainty component are set with respect to the color image data, the certainty of the oxygen saturation Sat calculated using a large value of the color image data for which there originally was no need to set the upper limit threshold value and a small value of the color image data for which there originally was no need to set the lower limit threshold value is set to be low, and thus there is a possibility that the state of the biological tissue T cannot be correctly determined based on the oxygen saturation distribution image.

Thus, in the present embodiment, in the case of setting the upper limit threshold value and the lower limit threshold value with respect to the component of the color image data to be used to calculate the oxygen saturation Sat, the upper limit threshold and the lower limit threshold are set with respect to components of different pieces of color image data, and therefore the certainty of the oxygen saturation Sat can be calculated efficiently using a large value of the color image data for which the upper limit value of the certainty component does not need to be set and a small value of the color image data for which the lower limit value of the certainty component does not need to be set.

In the examples shown in FIGS. 7 and 8, if the value of the component a of the color image data A is smaller than the lower limit threshold value of the certainty component included in the certainty, the certainty component based on the color image data A is set to rapidly change in a step-wise manner from 1, which is the certain value, to 0, and if the value of the component b of the color image data B is greater than the upper limit threshold value, the certainty component based on the color image data B is set to rapidly change in a step-wise manner from 1, which is the certain value, to 0. However, it is also preferable that the certainty of the oxygen saturation Sat is reduced gradually as the certainty shifts away from the threshold value due to the certainty component being set to be reduced gradually as the values of the components a and b of the color image data A and B shift away from the upper limit threshold value and the lower limit threshold value of the certainty components a and b of the color image data A and B.

The image display control unit 514 controls the display mode of the oxygen saturation distribution image according to the certainty of each pixel sent from the certainty calculation unit 511. It is preferable that, regarding the pixels for which the value of the certainty is lower than a pre-determined value, the image display control unit 514 changes the brightness, saturation, or hue of the pixels or changes the transparency of the pixels according to the values of the certainty. In this case, since it is possible to find out the level of certainty using the brightness, intensity, hue, or transparency, the operator can observe a highly-accurate pixel saturation distribution image with a visual distinction between low-certainty portions and the high-certainty portions.

It is also preferable that the image display control unit 514 displays an image of a distribution of the oxygen saturation Sat of a region located in a pre-set range of oxygen saturations superimposed on an image of the biological tissue T, and to adjust the transparency of the pixels according to the value of the certainty for the pixels with values of certainty that are lower than a pre-determined value. For example, it is preferable to increase the transparency of the pixels and make the image of the biological tissue T look more transparent the smaller the value of the certainty is.

Also, the image display control unit 514 preferably corrects the certainty such that if the first ratio used to obtain the amount of hemoglobin falls outside of a predetermined range, for example, a range that is not possible in actuality, the certainty of the oxygen saturation Sat decreases. In the embodiment above, Wide(Yh)/WL(R) or Wide(Yh)/{WL(R)+WL(G)} is used as the first ratio, and therefore if the first ratio falls outside of the predetermined range, there is a possibility that the first ratio itself is not a normal value. In this case, the image display control unit 514 preferably generates the certainty component based on the first ratio, and sets the certainty component to 0 if the first ratio exceeds the predetermined range, or determines the certainty component such that it gradually decreases as the degree of falling outside of the predetermined range increases. Accordingly, the certainty of the oxygen saturation Sat calculated based on the value of the first ratio, which has a possibility of not being a normal value, can be made lower. The certainty component based on this kind of first ratio is preferably further multiplied by the product of the certainty components determined based on the color image data to consolidate them into one corrected value of certainty. Accordingly, the certainty of the oxygen saturation Sat can be constituted such that the certainty of the oxygen saturation Sat decreases if the first ratio falls outside of the predetermined range.

The image display control unit 514 preferably controls the certainty such that the certainty decreases if the second ratio falls outside of a predetermined range. In the above-described embodiment, Narrow(Yh)/Wide(Yh) is used as the second ratio, and therefore if the second ratio exceeds the predetermined range, there is a possibility that the second ratio itself will not be a normal value. In this case, the image display control unit 514 preferably generates the certainty component based on the second ratio, and sets the certainty component to 0 if the second ratio exceeds the predetermined range, or determines the certainty component such that it gradually decreases as the degree of falling outside of the predetermined range increases. Accordingly, the certainty of the oxygen saturation Sat calculated based on the value of the second ratio, which has a possibility of not being a normal value, can be made lower. The certainty component based on this kind of second ratio is preferably further multiplied by the product of the certainty components determined based on the color image data to consolidate them into one corrected value of certainty. Accordingly, the certainty of the oxygen saturation Sat can be constituted such that the certainty of the oxygen saturation Sat decreases if the second ratio falls outside of the predetermined range.

Figure 10:
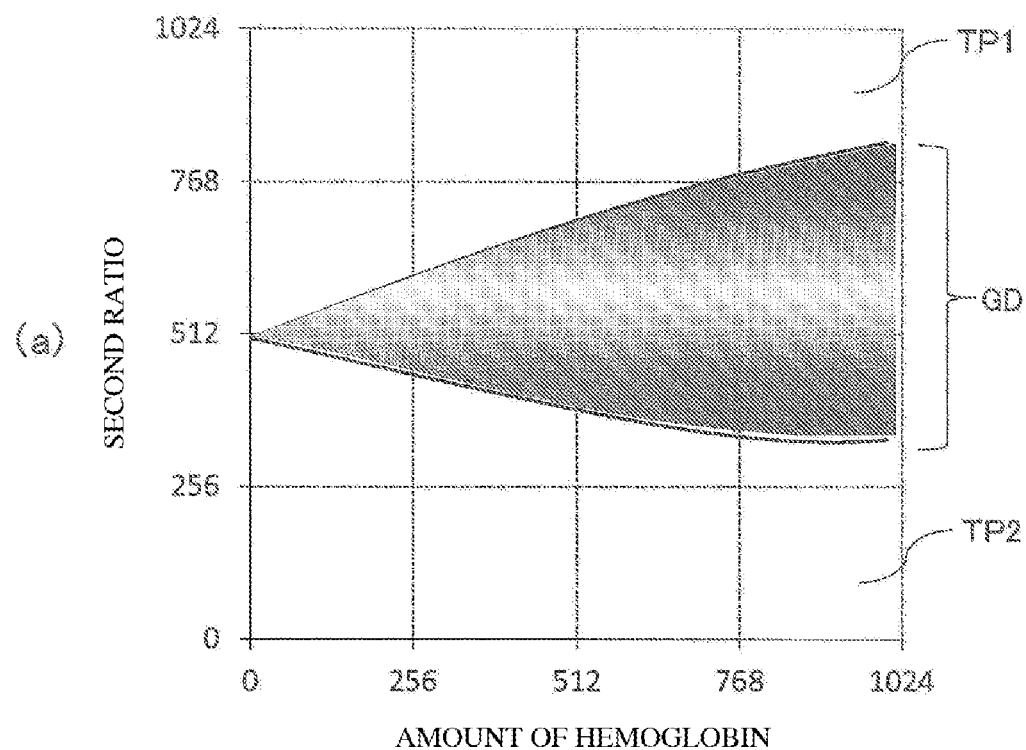
FIG. 10 is a diagram illustrating an example of an embodiment of an oxygen saturation distribution image of an embodiment.

Also, the image display control unit 514 preferably performs control such that the image of the distribution of the oxygen saturation Sat, for example, the image of the distribution of the oxygen saturation Sat in the set range of the oxygen saturation is displayed superimposed on the image of the biological tissue T, and performs control such that if the value of the second ratio falls outside of the allowed range as shown in FIG. 10, the transparency of the pixels is adjusted for the non-normal pixels that fall outside of the allowed range of the second ratio determined according to the amount of hemoglobin. Accordingly, display of the oxygen saturation Sat calculated based on the value of the second ratio, which has a possibility of not being a normal value, can be suppressed. In this case, it is also preferable to combine display with the control of the display mode for changing the brightness, saturation, or hue according to the certainty component based on the above-described second ratio.

FIG. 10 is a diagram for illustrating an example of a method for displaying an oxygen saturation distribution image in an embodiment. FIG. 10 shows an example of using transparent pixels with 100% transparency (in which the image of the underlayer looks completely transparent) for pixels that are located in the region in which the value of the second ratio exceeds the allowed range, which is interposed between curved lines in the drawing. GD is a region in the allowed region between the two curved lines and indicates the gradation pixel region in which the hue is changed according to the value of the oxygen saturation Sat. TP1 and TP2 are regions outside of the allowed region and indicate transparent pixel regions in which the pixels are transparent pixels with 100% transparency.

Also, the type of the color image data to be used in the upper limit threshold value and the lower limit threshold value of the above-described certainty component is not particularly limited, but in light of the fact that the appropriate certainty of the oxygen saturation Sat can be obtained, it is preferable that the upper limit threshold value of the certainty component is the value of the luminance component of the first color image data or the second color image data and that the lower limit threshold value of the certainty component is the value of the luminance component of the third color image data.

In the description above, it was described that the certainty of the oxygen saturation Sat is calculated when obtaining the amount of hemoglobin and the oxygen saturation Sat, but in the above-described embodiment at this time, three types of light with different wavelength bands are used as the illuminating light in order to obtain the amount of hemoglobin and the oxygen saturation Sat. However, it is also possible to obtain the amount of hemoglobin and the oxygen saturation Sat using the components of one piece of color image data obtained using one type of light instead of three types of light as the illuminating light. In this case, one type of light is used as the illuminating light, and therefore since the configuration of the light source apparatus 400 is simplified and there is no need to generate the multiple pieces of color image data, the configuration of the portions of the processor 200 is simplified.

In this case, for example, it is preferable that the light component (blue light component) of the wavelength band of 450 to 500 nm, the light component (green light component) of the wavelength band of 525 to 582 nm, and the light component (red light component) of the wavelength band of 620 to 670 nm are included in the one type of light. The three corresponding components of the color image data corresponding to the above-described light components can be obtained due to the color image data obtained with this kind of light being subjected to a matrix operation by the pre-image processing unit 504 shown in FIG. 1. In this case, according to an embodiment, the first ratio, which is an index for obtaining the amount of hemoglobin, can be the ratio of the corresponding component corresponding to the green light component with respect to the composite corresponding component obtained from the three corresponding components (e.g., a corresponding component having a value obtained by finding a weighted average of the values of the three corresponding components), and furthermore, the second ratio, which is an index for obtaining the oxygen saturation Sat, can be the ratio of the corresponding component corresponding to the blue light component with respect to the corresponding component corresponding to the green light component. In this embodiment as well, the certainty component can be obtained and the certainty of the oxygen saturation Sat can be calculated based on the values of the numerators and the denominators constituting the first ratio and the second ratio. That is, the light source apparatus 400 is configured to emit a first light including at least two light components with different wavelength bands. The pre-image processing unit 504 (corresponding component extraction unit) of the processor 200 extracts the corresponding component of the first color image data corresponding to each wavelength band of the light components from the first color image data generated in this manner by the electronic endoscope 100. The characteristic amount acquisition unit 510 acquires the oxygen saturation Sat of the hemoglobin as the characteristic amount of the biological tissue using at least the component a and the component b of the extracted corresponding components. For example, the first light to be used as an illuminating light to obtain the hemoglobin amount and the oxygen saturation Sat includes three light components, the hemoglobin amount calculation unit 510a of the characteristic amount acquisition unit 510 calculates the amount of hemoglobin based on the first ratio obtained using the corresponding components of the color image data corresponding to the wavelength bands of the three light components, and the oxygen saturation calculation unit 510b calculates the oxygen saturation Sat of the hemoglobin based on the amount of hemoglobin and the second ratio obtained using the corresponding components.

At this time, the certainty calculation unit 511 calculates the certainty in a state in which the first value of the component a of the corresponding components is set as the certainty lower limit threshold value and the second value of the component b is set as the certainty upper limit threshold value. At this time, the component a and the component b are two corresponding components that are different from each other. In this case, it is preferable to use the corresponding component that is to be the numerator of the first ratio as the component a for setting the certainty lower limit threshold value, and it is preferable to use the corresponding component that is to be the denominator of the first ratio as the component b for setting the certainty upper limit threshold value.

In this case as well, the certainty calculation unit 511 is configured to calculate the certainty for each pixel based on the certainty component obtained for each of the component a and the component b. At this time, if the value of the component a is greater than the certainty lower limit threshold value, the certainty component obtained from the component a preferably includes a value that is the same as or greater than the certainty component of the certainty lower limit threshold value, and if the value of the component b is smaller than the certainty upper limit threshold value, the certainty upper limit threshold value obtained from the component b preferably includes a value that is the same as or greater than the certainty component of the threshold upper limit threshold value. In this manner, the certainty upper limit threshold value and the certainty lower limit threshold value are set for different corresponding components of the color image data, and therefore the certainty of the oxygen saturation Sat can be efficiently calculated using a large value of the color image data for which the upper limit threshold value of the certainty component does not need to be set and a small value of the color image data for which the lower limit threshold value of the certainty component does not need to be set.

According to an embodiment, if the first light having three light components with different wavelength bands is used as the illuminating light in order to obtain the amount of the hemoglobin and the oxygen saturation Sat, the light source apparatus 400 preferably emits the first light and the second light, which has a different wavelength band from the first light, as well. In this case, it is also preferable that the hemoglobin amount calculation unit 510*a* calculates the amount of hemoglobin based on the first ratio of the components a and b corresponding to the wavelength bands of the light components extracted from the first color image data generated when the first light is used as the illuminating light, and that the oxygen saturation calculation unit 510*b* generates the second ratio based on one of the component a and the component b and one component of the second color image data generated when the second light is used as the illuminating light, and calculates the oxygen saturation Sat of the hemoglobin based on the second ratio and the amount of hemoglobin calculated by the hemoglobin amount calculation unit 510*a*.

For example, a light component (blue light component) in the wavelength band of 450 to 500 nm, a light component (green light component) in the wavelength band of 525 to 582 nm, and a light component (red light component) in the wavelength band of 620 to 670 nm are included in the first light. The wavelength band of the second light is 545 to 570 nm.

In this case, according to an embodiment, the first ratio, which is an index for obtaining the amount of hemoglobin, can be the ratio of the corresponding component corresponding to the green light component of the corresponding component with respect to the sum of the corresponding component corresponding to the green light component and the corresponding component corresponding to the red light component, that is, the composite corresponding component, and the second ratio, which is an index for obtaining the oxygen saturation Sat can be the ratio of the component corresponding to the wavelength band of 545 to 570 nm in the second color image data with respect to the corresponding component corresponding to the green light component of the second color image data.

In the above-described embodiment, in order to perform highly-accurate diagnosis using the endoscope system 1, it is required that the oxygen saturation distribution image indicating the distribution of the oxygen saturation Sat has high image quality. For this reason, the oxygen saturation distribution image preferably has 1 million pixels or more, more preferably 2 million pixels or more, and even more preferably 8 million pixels or more. On the other hand, the greater the number of pixels in the image being handled is, the larger the arithmetic circuit of the processor 200 tends to be, and the greater the processing load also tends to be. In particular, with a high number of pixels (high image quality) of 1 million pixels or more, the above-described tendency is prominent. In an embodiment, as described above, a reference table in which the amount of hemoglobin, the oxygen saturation Sat, and the color image data is associated, and information on the correlation are obtained in advance, and the amount of hemoglobin and the oxygen saturation Sat are calculated using the reference table and the correlation, and therefore in the above-described embodiment, the amount of hemoglobin and the oxygen saturation Sat can be calculated efficiently compared to the case of calculating the amount of hemoglobin and the oxygen saturation each time the color image data is acquired and without using the reference table and the correlation. For this reason, the arithmetic circuit of the processor 200 can be made smaller, and thus a processor 200 with a low cost, low heat generation, and low power consumption can be provided even if an image with high image quality is to be generated.

In the above description, an embodiment has been described, but the present disclosure is not limited to the above-described configuration, and various modifications are possible within the range of the technical idea of the present disclosure.

REFERENCE SIGNS LIST

1 Endoscope system
100 Electronic endoscope
110 Insertion tube
111 Insertion tube leading end portion
121 Object lens group
131 Light guide
131*a* Leading end portion
131*b* Base end portion
132 Lens
141 Image sensor
141*a* Color filter
142 Cable
200 Processor
300 Display
400 Light source apparatus
410 Rotating filter 420 Filter control unit
430 Light source lamp
440 Light condensing lens
450 Light condensing lens
500 Image processing unit
502 A/D conversion circuit
504 Pre-image processing unit
506 Frame memory unit
508 Post-image processing unit
510 Characteristic amount acquisition unit
511 Certainty calculation unit
512 Memory
514 Image display control unit
516 Controller

The invention claimed is:

1. An endoscope system comprising:
a light source apparatus configured to emit at least two types of light with different wavelength bands;
an endoscope including an imaging unit that includes an image sensor configured to generate a plurality of pieces of color image data corresponding to the at least two types of light by imaging biological tissue illuminated with the at least two types of light;
a processor including: a characteristic amount acquisition unit configured to acquire an oxygen saturation of hemoglobin in the biological tissue as a characteristic amount of the biological tissue using at least a component a and a component b among components of the color image data, and to generate an oxygen saturation distribution image showing a distribution of the characteristic amount; a certainty calculation unit configured to calculate a certainty of the characteristic amount using the components of the color image data; and an image display control unit configured to control a mode of displaying the oxygen saturation distribution image according to a result of calculating the certainty; and
an image display apparatus configured to display the oxygen saturation distribution image,
wherein the certainty calculation unit is configured to calculate the certainty in a state in which a first value of a component a of color image data A is set as a certainty lower limit threshold value at which the certainty falls below the certainty at a value greater than or equal to the first value if the value of the component a of the color image data A is lower than the first value, and a second value, which is greater than the first value, of a component b of color image data B of the color image data is set as a certainty upper limit threshold value at which the certainty falls below the certainty at a value less than or equal to the second value if the value of the component b of the color image data B is greater, and the color image data A and the color image data B are pieces of color image data corresponding to the two different types of light.

2. The endoscope system according to claim 1, wherein the certainty calculation unit is configured to calculate the certainty for each pixel based on certainty components based on each of the component a and the component b,
if the value of the component of the color image data A is greater than the certainty lower limit threshold value, the certainty component obtained based on the color image data A has a value that is the same as or greater than the certainty component at the certainty lower limit threshold value, and
if the value of the component of the color image data B is smaller than the certainty upper limit threshold value, the certainty component obtained based on the color image data B has a value that is the same as or greater than the certainty at the certainty upper limit threshold value.

3. The endoscope system according to claim 1, wherein the characteristic amount acquisition unit includes: a hemoglobin amount calculation unit configured to calculate an amount of hemoglobin based on a first ratio obtained using a component including at least one of the component a and the component b of the color image data; and an oxygen saturation calculation unit configured to calculate an oxygen saturation of the hemoglobin based on the amount of hemoglobin and a second ratio obtained using a component including at least one of the component a and the component b of the color image data, and
the certainty calculation unit is configured to perform correction such that the certainty decreases when the first ratio falls outside of a predetermined range.

4. The endoscope system according to claim 1, wherein the characteristic amount acquisition unit includes: a hemoglobin amount calculation unit configured to calculate an amount of hemoglobin based on a first ratio obtained using a component including at least one of the component a and the component b of the color image data; and an oxygen saturation calculation unit configured to calculate an oxygen saturation of the hemoglobin based on the amount of hemoglobin and a second ratio obtained using a component including at least one of the component a and the component b of the color image data, and
the certainty calculation unit is configured to perform correction such that the certainty decreases when the second ratio falls outside of a predetermined range.

5. The endoscope system according to claim 3, wherein the image display control unit performs control such that the image of the distribution of the characteristic amount is displayed superimposed on the image of the biological tissue, and is configured to adjust a transparency of a pixel in which the value of the second ratio falls outside of an allowable range of the second ratio determined according to the amount of hemoglobin.

6. The endoscope system according to claim 3, wherein the light source apparatus is configured to emit at least three or more types of light including a first light, a second light, and a third light with different wavelength bands,
the imaging unit is configured to generate first color image data corresponding to the first light, second color image data corresponding to the second light, and third color image data corresponding to the third light by imaging biological tissue illuminated with the first light, the second light, and the third light,
the first ratio is a ratio between one component of the first color image data and one component of the second color image data, and
the second ratio is a ratio between one component of the second color image data and one component of the third color image data.

7. The endoscope system according to claim 6, wherein the wavelength band of the first light is wider than the wavelength band of the second light and the wavelength band of the third light, and the wavelength band of the second light is wider than the wavelength band of the third light, and the certainty upper limit threshold value is a value of a luminance component of the first color image data or the second color image data, and the certainty lower limit threshold value is a value of a luminance component of the third color image data.

8. The endoscope system according to claim 6, wherein the first ratio is a ratio between a luminance component of the second color image data and an R component or a sum of an R component and a G component of the first color image data, and
the hemoglobin amount calculation unit calculates the amount of the hemoglobin based on the first ratio.

9. The endoscope system according to claim 6, wherein the second ratio is a ratio between a luminance component of the third color image data and a luminance component of the second color image data, and
the oxygen saturation calculation unit calculates the oxygen saturation of the hemoglobin based on the second ratio and the amount of hemoglobin.

10. The endoscope system according to claim 6, wherein in the wavelength band of the second light, a component of the second color image data includes a wavelength band that is sensitive to change in the hemoglobin amount of the biological tissue but is not sensitive to change in the oxygen saturation.

11. The endoscope system according to claim 6, wherein in the wavelength band of the third light, a component of the third color image data includes a wavelength band that is sensitive to change in the oxygen saturation.

12. The endoscope system according to claim 6, wherein the second light is filtered light of the first light, obtained by an optical filter allowing transmission of a first wavelength band in a range of 500 nm to 600 nm in the wavelength band of the first light, and the third light is filtered light of the first light, obtained by an optical filter allowing transmission of a second wavelength band that is narrower than the first wavelength band in the range of the first wavelength band.

13. An endoscope system comprising:
a light source apparatus configured to emit a first light including at least two light components with different wavelength bands;
an endoscope including an imaging unit that includes an image sensor configured to generate first color image data by imaging biological tissue illuminated with the first light;
a processor including: a characteristic amount acquisition unit configured to acquire an oxygen saturation of hemoglobin in the biological tissue as a characteristic amount of the biological tissue using at least a component a and a component b among corresponding components of the first color image data, which correspond to respective wavelength bands of the light components, and to generate an oxygen saturation distribution image showing a distribution of the characteristic amount; a certainty calculation unit configured to calculate a certainty of the characteristic amount using the corresponding components of the color image data; and an image display control unit configured to control a mode of displaying the oxygen saturation distribution image according to a result of calculating the certainty; and
an image display apparatus configured to display the oxygen saturation distribution image,
wherein the certainty calculation unit is configured to calculate the certainty in a state in which a first value of the component a is set as a certainty lower limit threshold value at which the certainty falls below the certainty at a value greater than or equal to the first value if the value of the component a is lower than the first value, and a second value, which is greater than the first value, of the component b is set as a certainty upper limit threshold value at which the certainty falls below the certainty at a value less than or equal to the second value if the value of the component b is greater, and the component a and the component b are two corresponding components that are different from each other.

14. The endoscope system according to claim 13, wherein the certainty calculation unit is configured to calculate the certainty for each pixel based on certainty components based on each of the component a and the component b,
if the value of the component a is greater than the certainty lower limit threshold value, the certainty component obtained based on the component a has a value that is the same as or greater than the certainty component at the certainty lower limit threshold value, and
if the value of the component b is smaller than the certainty upper limit threshold value, the certainty component obtained based on the component b has a value that is the same as or greater than the certainty component at the certainty upper limit threshold value.

15. The endoscope system according to claim 13, wherein the light source apparatus is configured to emit a second light with a different wavelength band from the first light, in addition to the first light,
the imaging unit is configured to generate the first color image data and second color image data corresponding to the second light by imaging the biological tissue illuminated with the first light and the second light, and
the characteristic amount acquisition unit includes: a hemoglobin amount calculation unit configured to calculate an amount of hemoglobin based on a first ratio of the component a and the component b; and an oxygen saturation calculation unit configured to calculate the oxygen saturation of the hemoglobin based on the amount of hemoglobin and a second ratio between one of the component a and the component b and a component of the second color image data.

16. The endoscope system according to claim 13, wherein the first light includes three light components, and
the characteristic amount acquisition unit includes: a hemoglobin amount calculation unit configured to calculate an amount of hemoglobin based on a first ratio obtained using the corresponding components; and an oxygen saturation calculation unit configured to calculate the oxygen saturation of the hemoglobin based on the amount of hemoglobin and a second ratio obtained using the corresponding components.

17. A method of analyzing biological tissue comprising:
emitting a first light including at least two light components with different wavelength bands;
generating first color image data by imaging biological tissue illuminated with the first light;
using at least a component a and a component b among corresponding components of the first color image data, which correspond to respective wavelength bands of the light components, to acquire an oxygen saturation of hemoglobin in the biological tissue as a characteristic amount of the biological tissue;
generating an oxygen saturation distribution image showing a distribution of the characteristic amount;

calculating a certainty of the characteristic amount using the corresponding components of the color image data; and controlling a mode of displaying the oxygen saturation distribution image according to a result of calculating the certainty, wherein the calculated certainty is lower if a value of the component a is lower than a certainty lower limit threshold value than if the value of the component a is higher than the certainty lower limit threshold value, and wherein the calculated certainty is lower if a value of the component b is higher than a certainty upper limit threshold value than if the value of the component b is lower than the certainty upper limit threshold value, and wherein the component a and the component b are two corresponding components that are different from each other.

18. The method according to claim 17, wherein the calculating a certainty comprises calculating a certainty for each of a plurality of pixels of the first color image data, based on a certainty component that is based on the component a and a certainty component that is based on the component b, and wherein, if the value of the component a is greater than the certainty lower limit threshold value, the certainty component obtained based on the component a has a value that is the same as or greater than the certainty component at the certainty lower limit threshold value, and wherein, if the value of the component b is smaller than the certainty upper limit threshold value, the certainty component obtained based on the component b has a value that is the same as or greater than the certainty component at the certainty upper limit threshold value.

19. The method according to claim 17, the method further comprising:

emitting a second light with a different wavelength band from the first light;

generating second color image data corresponding to the second light by imaging the biological tissue illuminated with the second light;

calculating an amount of hemoglobin based on a first ratio of the component a and the component b; and calculating the oxygen saturation of the hemoglobin based on the calculated amount of hemoglobin and a second ratio between one of the component a and the component b and a component of the second color image data.

20. The method according to claim 17, wherein the first light includes three light components, and wherein the method includes:

calculating an amount of hemoglobin based on a first ratio obtained using the corresponding components; and calculating the oxygen saturation of the hemoglobin based on the calculated amount of hemoglobin and a second ratio obtained using the corresponding components.

* * * * *